(12) United States Patent
Bretting

(10) Patent No.: US 6,573,255 B1
(45) Date of Patent: Jun. 3, 2003

(54) VITAMIN D ANALOGUES

(75) Inventor: Claus Aage Svensgaard Bretting, Frederiksberg (DK)

(73) Assignee: Leo Pharmaceutical Products Ltd., A/S, Ballerup (DK)

( * ) Notice: Subject to any disclaimer, the term of this patent is extended or adjusted under 35 U.S.C. 154(b) by 0 days.

(21) Appl. No.: 10/048,363

(22) PCT Filed: Jul. 11, 2000

(86) PCT No.: PCT/DK00/00389

§ 371 (c)(1),
(2), (4) Date: Feb. 1, 2002

(87) PCT Pub. No.: WO01/10829

PCT Pub. Date: Feb. 15, 2001

Related U.S. Application Data

(60) Provisional application No. 60/147,200, filed on Aug. 4, 1999.

(51) Int. Cl.[7] ........................ A61K 31/59; C07C 401/00

(52) U.S. Cl. ........................................ 514/167; 552/653

(58) Field of Search ............................ 552/653; 514/167

(56) References Cited

U.S. PATENT DOCUMENTS 5,446,034 A * 8/1995 Bretting et al.
6,207,656 B1 * 3/2001 Carswell et al. ............ 514/167

FOREIGN PATENT DOCUMENTS

WO   WO 93/19044 A1   9/1993

* cited by examiner

*Primary Examiner*—Sabiha Qazi
(74) *Attorney, Agent, or Firm*—Birch, Stewart, Kolasch & Birch, LLP

(57) ABSTRACT

Vitamin D compounds formula I wherein R represents hydrogen, or R represents $(C_1-C_6)$ alkyl, phenyl, or $(C_7-C_9)$aralkyl, optionally substituted with one or more groups selected from $(C_1-C_3)$alkyl, F, phenyl; n is an integer having the value 0, 1, or 2; and X represents hydroxy or halogen.

14 Claims, No Drawings

VITAMIN D ANALOGUES

This application is the national phase under 35 U.S.C. § 371 of PCT International Application No. PCT/DK00/00389 which has an International filing date of Jul. 11, 2000, which designated the United States of America and was published in English and claims the benefit of Provisional application No. 60/147,200, filed Aug. 4, 1999.

FIELD OF THE INVENTION

This invention relates to a hitherto unknown class of compounds that show strong activity in inducing differentiation and inhibiting undesirable proliferation of certain cells, including skin cells and cancer cells, as well as immunomodulating and antiinflammatory effects, to pharmaceutical preparations containing these compounds, to dosage units of such preparations, and to their use in the treatment and/or prophylaxis of diseases characterized by abnormal cell differentiation and/or cell proliferation.

BACKGROUND OF THE INVENTION

A number of vitamin D analogues have been described that show some degree of selectivity in favour of the cell differentiation inducing/cell proliferation inhibiting activity in vitro as compared to the effects on calcium metabolism in vivo (as measured in increased serum calcium concentration and/or increased urinary calcium excretion), which adversely limit the dosage that can safely be administered to patients. One of the first of these to appear, calcipotril (INN) or calcipotriene (USAN), has been developed on the basis of this selectivity and is now recognized worldwide as an effective and safe drug for the topical treatment of psoriasis.

A study with another vitamin D analogue, seocalcitol, selected on this basis supports the concept that systemically administered vitamin D analogues may inhibit breast cancer cell proliferation in vivo at sub-toxic doses (Colston, K. W. et al., Biochem. Pharmacol. 44, 2273–2280 (1992)).

Another vitamin D analogue, CB1093 (20-epi-22-ethoxy-23-yne-24a, 26a, 27a, trishomo-1α,25(OH)$_2$D$_3$ vitamin D$_3$) (Calverley M. J. et al. In: Vitamin D, Proceedings of the Ninth Workshop on Vitamin D, Orlando, Fla., Walter de Gruyter, Berlin, 1994, pp 85–86; and disclosed in WO 93/19044) has been shown to possess potent activity in an in vitro assay on inhibiting the invasiveness of human carcinoma cells (Hansen C. M. et al. In: Vitamin D, Proceedings of the Ninth Workshop on Vitamin D, Orlando, Fla., Walter de Gruyter, Berlin, 1994, pp 508–509).

CB1093 has also been demonstrated to have potent inhibitory activity on the proliferation of, and stimulatory activity on the differentiation and apoptosis of, different types of cancer cells, such as, brain glial tumor cells in vitro (Baudet, C. et al., Cancer Lett. 1996, 100, 3); MCF-7 breast cancer cells in vitro and in vivo (Colston, K. W., et al., In: Vitamin D, Proceedings of the Tenth Workship on Vitamin D, Strasbourg, France, 1997, University of California, Riverside, 1997, pp 443–450; Danielsson, C. et al., In: Vitamin D, Proceedings of the Tenth Workshop on Vitamin D, Strasbourg, France, 1997, University of California, Riverside, 1997, pp 485–486; Danielsson, C. et al., J. Cellular Biochem., 1997, 66, 552); NB4 acute promyelocytic leukemia cells in vitro (Elstner, E., et al., J. Clin. Invest., 1997, 99, 349); HL-60 and de novo human acute myeloid leukemia cells in vitro (Pakkala, I. et al., Blood 1995, 86(10, Suppl.), 775a; Pakkala, I. et al., Leukemia Research 1997, 21, 321); and MG-63 human osteosarcoma cells in vitro (Ryhänen, S., et al., J. Cellular Biochem. 1998, 70, 414).

CB 1093 also significantly decreased plasma PTH and phosphate levels in chronically uraemic rats with secondary hyperparathyroidism (Hruby, M. et al., Nephrol. Dial. Transplant. 1996, 11, 1781).

The classical calcemic vitamin D activity of CB1093, as determined by the urinary excretion of calcium in rats, has been determined to 27% of that of 1α,25(OH)$_2$D$_3$ and the calcemic activity of seocalcitol in the same assay has been determined to 50% (Danielsson, C. et al., J. Cellular Biochem., 1997, 66, 552). In an in vivo experiment treating rats with mammary tumours with CB1093 (1 μg/kg body weight for 28 days) there was a 49% reduction of the initial tumour volume, but there was still a slight increase in the serum calcium concentration (ibid.). This indicates that the therapeutic window may still be rather narrow, and concern about possible induced increases in serum calcium levels cannot yet be excluded.

Another problem using vitamin D analogues in the non-topical treatment of hyperproliferative diseases, such as cancer, is metabolic stability in vivo. This stability has to be above a certain minimum level, for a compound to be used in practical therapy. As shown in table 1, the stability of CB1093 in an in vitro-model of metabolic stability, using rat liver homogenate "S-9" (Kissmeyer, A.-M. et al., Biochem. Pharmacol., 1997, 53, 1087) is quite low compared to seocalcitol (T½ 1.3 hr) and 1α,25(OH)$_2$D$_3$ (T½ 2.5 hr).

There is therefore a continuing need for new vitamin D analogues with high anti-cell proliferative and/or cell differentiation inducing activity showing an acceptable combination of prolonged therapeutic activity and minimum toxic effects compared to 1α,25(OH)$_2$D$_3$. The purpose of the present invention is to provide such new compounds, which purpose is achieved with the novel compounsd having the general formula I herein.

SUMMARY OF THE INVENTION

The compounds of the invention constitute a novel class of vitamin D analogues represented by the general formula I:

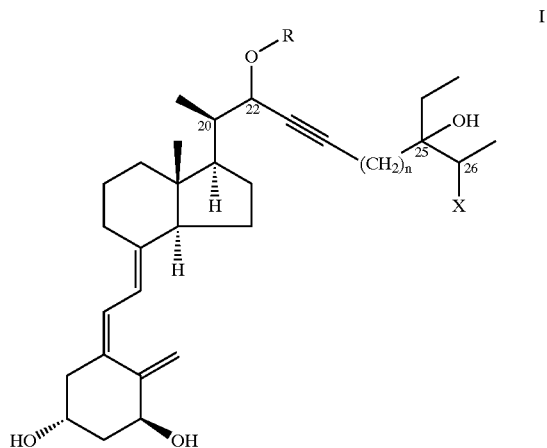

wherein formula R represents hydrogen, or (C$_1$–C$_6$)alkyl, phenyl, or (C$_7$–C$_9$)aralkyl optionally substituted with one or more of (C$_1$–C$_3$)alkyl, F, or phenyl; n is an integer having the value 0, 1, or 2; and X represents hydroxy or halogen.

DETAILED DESCRIPTION OF THE INVENTION

Preferred embodiments of the invention.

Preferred compounds of formula I are compounds wherein R represents methyl, ethyl, propyl, isopropyl, benzyl, and ortho methylbenzyl, meta methylbenzyl, and para methylbenzyl. More preferably R represents methyl or ethyl. n is preferably 0 or 1; 1 being more preferred. Preferably X represents OH, F, or Cl. Most preferably X represents F or X most preferably represents OH or Cl.

The compounds of the invention can comprise more than one diastereoisomeric form; that is both R and S configurations at the carbon atoms marked 22, 25 and 26 in formula I. The invention covers all these diastereoisomers in pure form and also mixtures thereof. Preferred isomers are compounds having the configurations 22(S),25(S),26(S) and 22(S),25(S),26(R). In addition, prodrugs of compounds of formula I in which one or more of the hydroxy groups are masked as groups that can be reconverted to hydroxy groups in vivo could also be envisaged.

The compounds I may be obtained in crystalline form either directly by concentration from an organic solvent or by crystallisation or recrystallisation from an organic solvent or mixture of said solvent and a co-solvent which may be organic or inorganic, such as water. The crystals may be isolated in essentially solvent-free form or as a solvate, such as a hydrate. The invention covers all crystalline modifications and forms and also mixtures thereof.

Exemplary compounds of the invention are

1(S),3(R)-Dihydroxy-20(R)-(5-ethyl-1(S),5(S),6(S)-trihydroxy-2-heptyn-1-yl)-9,10-secopregna-5(Z),7(E),10(19)-triene (Compound 101), 1(S),3(R)-Dihydroxy-20(R)-(5(S),6(S)-dihydroxy-5-ethyl-1(S)-methoxy-2-heptyn-1-yl)-9,10-secopregna-5(Z),7(E),10(19)-triene (Compound 102), 1(S),3(R)-Dihydroxy-20(R)-(5(S),6(S)-dihydroxy-1(S)-ethoxy-5-ethyl-2-heptyn-1-yl)-9,10-secopregna-5(Z),7(E),10(19)-triene (Compound 103), 1(S),3(R)-Dihydroxy-20(R)-(5(S),6(S)-dihydroxy-5-ethyl-1(S)-(1-propyloxy)-2-heptyn-1-yl)-9,10-secopregna-5(Z),7(E),10(19)-triene (Compound 104), 1(S),3(R)-Dihydroxy-20(R)-(1(S)-benzylyloxy-5(S),6(S)-dihydroxy-5-ethyl-2-heptyn-1-yl)-9,10-secopregna-5(Z),7(E),10(19)-triene (Compound 105), 1(S),3(R)-Dihydroxy-20(R)-(5(R),6(S)-dihydroxy-1(S)-ethoxy-5-ethyl-2-heptyn-1-yl)-9,10-secopregna-5(Z),7(E),10(19)-triene (Compound 106), 1(S),3(R)-Dihydroxy-20(R)-(5(R),6(R)-dihydroxy-1(S)-ethoxy-5-ethyl-2-heptyn-1-yl)-9,10-secopregna-5(Z),7(E),10(19)-triene (Compound 107), 1(S),3(R)-Dihydroxy-20(R)-(5(S),6(R)-dihydroxy-1(S)-ethoxy-5-ethyl-2-heptyn-1-yl)-9,10-secopregna-5(Z),7(E),10(19)-triene (Compound 108), (S),3(R)-Dihydroxy-20(R)-(4-ethyl-1(S),4(S),5(S)-trihydroxy-2-hexyn-1-yl)-9,10-secopregna-5(Z),7(E),10(19)-triene (Compound 109), (S),3(R)-Dihydroxy-20(R)-(4(S),5(S)-dihydroxy-1(S)-ethoxy 4 ethyl 2 hexyn-1-yl)-9,10-secopregna-5(Z),7(E),10(19)-triene (Compound 111), 1(S),3(R)-Dihydroxy-20(R)-(4-ethyl-1(S),4(R),5(S)-trihydroxy-2-hexyn-1-yl)-9,10-secopregna-5(Z),7(E),10(19)-triene (Compound 114), 1(S),3(R)-Dihydroxy-20(R)-(4(R),5(S)-dihydroxy-1(S)-ethoxy-4-ethyl-2-hexyn-1-yl)-9,10-secopregna-5(Z),7(E),10(19)-triene (Compound 116), 1(S),3(R)-Dihydroxy-20(R)-(1(S)-ethoxy-5-ethyl-6(S)-fluoro-5(S)-hydroxy-2-heptyn-1-yl)-9,10-secopregna-5(Z),7(E),10(19)-triene (compound 149), and 1(S),3(R)-Dihydroxy-20(R)-(1(S)-ethoxy-5-ethyl-6(R)-fluoro-5(S)-hydroxy-2-heptyn-1-yl)-9,10-secopregna-5(Z),7(E),10(19)-triene (compound 150).

1(S),3(R)-Dihydroxy-20(R)-(1(S),5(R/S)-dihydroxy-5-ethyl-6(S)-fluoro-2-heptyn-1-yl)-9,10-secopregna-5(Z),7(E),10(19)-triene (compound 157)

1(S),3(R)-Dihydroxy-20(R)-(1(S)-ethoxy 5-ethyl-6(S)-fluoro-2-heptyn-5(R/S)-hydroxy 1-yl)-9,10-secopregna-5(Z),7(E),10(19)-triene (compound 158)

1(S),3(R)-Dihydroxy-20(R)-(1(S),5(R/S)-dihydroxy-5-ethyl-6(R)-fluoro-2-heptyn-1-yl)-9,10-secopregna-5(Z),7(E),10(19)-triene (compound 159)

1(S),3(R)-Dihydroxy-20(R)-(1(S)-ethoxy 5-ethyl-6(R)-fluoro-2-heptyn-5(R/S)-hydroxy 1-yl)-9,10-secopregna-5(Z),7(E),10(19)-triene (compound 160)

As used in the specification the following terms have the meaning indicated:

"Alkyl" refers to any univalent group derived from an alkane by removal of a hydrogen atom from any carbon atom, and includes the subclasses of normal alkyl (n-alkyl), and primary, secondary and tertiary alkyl groups respectively, and having the number of carbon atoms specified, including for example $(C_1–C_3)$alkyl, $(C_1–C_6)$ alkyl, methyl, ethyl, n-propyl, isopropyl, n-butyl, isobutyl, sec-butyl, t-butyl, n-pentyl, and n-hexyl. Alkane refers to an acyclic straight or branched hydrocarbon having the general formula $C_nH_{2n+2}$, and therefore consisting entirely of hydrogen atoms and saturated carbon atoms.

"$(C_7–C_9)$aralkyl" refers to any alkyl group substituted with an aromatic group, such as phenyl, and having the total number of carbon atoms specified, preferred are $(C_7–C_8)$ aralkyl groups. Examples are benzyl, 2-phenyl-ethyl, ortho methylbenzyl, meta methylbenzyl, and para methylbenzyl.

"Halogen" means the same or different of fluoro, chloro, bromo, and iodo.

The present invention provides a hitherto undisclosed series of vitamin D analogues which is characterised by the presence of an additional hydroxy group or halogen atom in the 26 position of the side chain. Compared to the prior art vitamin D analogues, illustrated by CB1093, the present new vitamin D analogues have precisely the properties which are demanded (Table 1): Half or less the calcemic activity (in the rat calciuric model) and much higher metabolic stability (in the S-9 rat liver homogenate model), together with an only slightly reduced antiproliferative activity (in two different cancer assays: The U937 leukemia cell assay (Kissmeyer, A.-M. et al., *Biochem. Pharmacol.*, 1997, 53, 1087) and the MCF-7 mammary cancer cell assay (Danielsson, C. et al., *J. Cellular Biochem.*, 1997, 66, 552)). Moreover the activity of the present Compounds I in the HaCaT assay, a psoriasis model (Kissmeyer, A.-M. et al., *Biochem. Pharmacol.*, 1997, 53, 1087), is slightly higher than that of CB1093. The advantageous properties of the 26-hydroxy or 26-halogen vitamin D analogues of the present invention are entirely unexpected, as it is known that a similar introduction of a 26-hydroxy group in seocalcitol results in compounds with drastically reduced activities in both the U937 and the HaCaT assays. All the four possible 26-hydroxy-seocalcitol analogues have been shown to be natural metabolites of seocalcitol in vitro and in vivo in rats and in vitro in humans (Binderup, E., et al., In: Vitamin D, Proceedings of the Tenth Workshop on Vitamin D, Strasbourg, France, 1997, University of California, Riverside, 1997, pp 89–90; Kissmeyer, A.-M. et al., *Biochem. Pharmacol.*, 1997, 53, 1087).

TABLE 1

| Compound 25/26-Configur. Assay | 1α, 25(OH)$_2$D$_3$ | No. 103 §<br>25(S), 26(S) | No. 108 §<br>25(S), 26(R) | CB1093 §, $<br>(No 26-OH) |
|---|---|---|---|---|
| U937, -log IC$_{50}$ | 7.5 ± 0.3 | 9.0 ± 0.2 | 8.9 ± 0.2 | 9.5 ± 0.1 |
| U937, rel.* | 1.0 | 36 | 49 | 74 |
| MCF-7, -log IC$_{50}$ | 7.7 ± 0.3 | 9.9 ± 0.1 | 9.8 ± 0.2 | 10.2 ± 0.3 |
| MCF-7, rel.* | 1.0 | 153 | 89 | 311 |
| HaCaT, -log IC$_{50}$ | 7.4 ± 0.3 | 9.0 ± 0.3 | 8.8 ± 0.2 | 8.7 ± 0.9 |
| HaCaT, rel.* | 1.0 | 38 | 30 | 18 |
| S-9, metab. in vitr. # | | 0.43 | 0.29 | 0.02 |
| Calcem.; in vivo* | 1.0 | 0.11 | 0.6 | 0.27 |

Notes to Table 1:
§ R = Ethyl, n = 1 and 22(S)-configuration
$ Reference compound: No 26-OH-group; otherwise the same structure as Compound 103/108
*Geometric mean of the ratios, relative to 1α, 25(OH)$_2$D$_3$, from all experiments with the compound in question, in the assay concerned; the higher the value, the more potent the compound
Fraction left after 1 hour incubation The following standard abbreviations are used throughout this disclosure:
AcOH=acetic acid
18C6=18-Crown-6
b.p.=boiling point
Bn=benzyl
Bu=n-butyl
Comp=Compound No.
DMAP=4-dimethylaminopyridine
DMF=N,N-dimethylformamide
Et=ethyl
EtOAc=ethyl acetate
Exam=Example No.
eqv=equivalent (molar)
Ether=diethyl ether
G.P.=General Procedure No.
Hal=Cl, Br or I
h=hour
Me=methyl
m.p.=melting point
Ms=methanesulfonate
PG=Protective Group
Ph=phenyl
Pr=n-propyl
Prep=Preparation No.
PPTS=pyridinium p-toluenesulfonate
Py=pyridine
TBAF=tetra-n-but
Compounds of formula I, as illustrated in Table 4, may be prepared by the general method of Scheme 1: ylammonium fluoride
TBS=tert butyldimethylsilyl
Tf=trifluromethanesulfonyl
THF=tetrahydrofuran
THP=tetrahydro-4H-pyran-2-yl
TMS=trimethylsilyl
Tol=toluene
Ts=4-toluenesulfonyl Compounds of formula I, as illustrated in Table 4, may be prepared by the general method of Scheme 1:

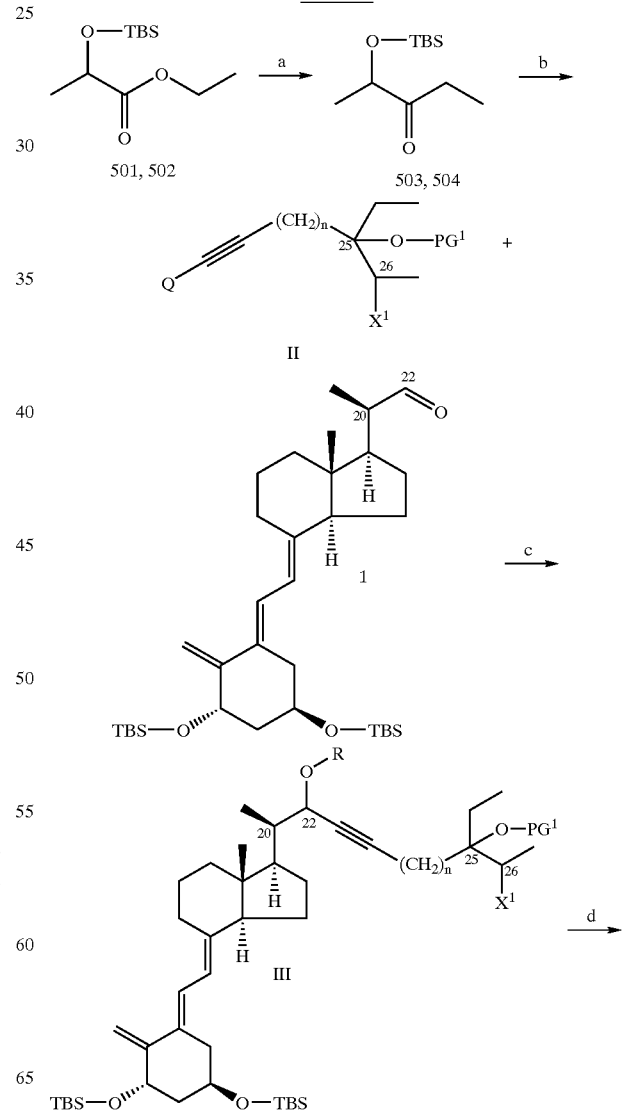

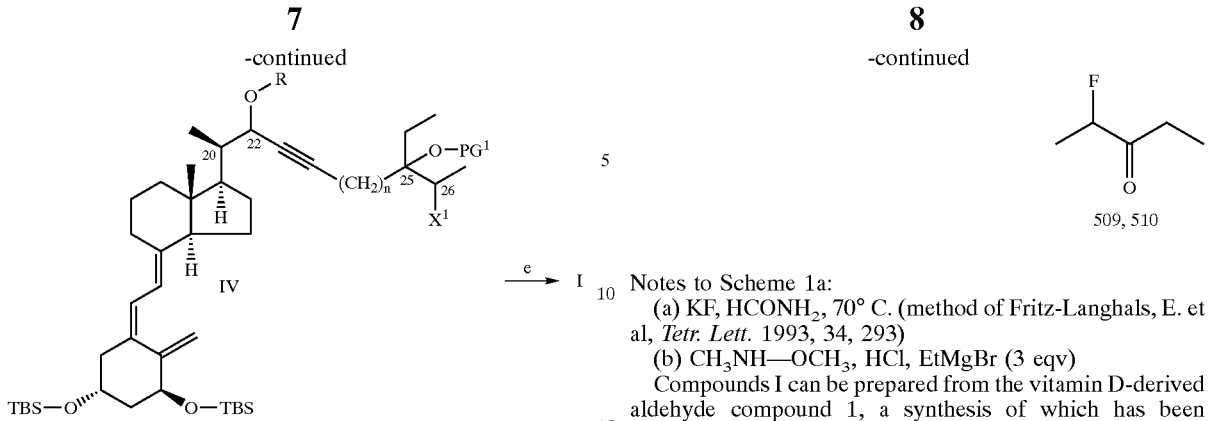

Notes to Scheme 1:
General: $X^1$=O-$PG^2$, F, Cl, Br, or I
$PG^1$ and $PG^2$=Hydrogen or Protective Groups: the same or different, or a combined bifunctional group.
Q=H or $Me_3Si$; n=1,2 or 3.

(a) $CH_3NH$—$OCH_3$, HCl; EtMgBr (3 eqv)
(b) i) Q-C≡C—$(CH_2)_n$-Met; (Met=-Li, -MgHal; -$AlBr_2$, -Br+$SmI_2$);
  if it is desired (only for Q=H) that: $PG^1$=TMS and $X^1$=O-$PG^1$=O-TBS and Q=H;
  ii) $Me_3SiCl/Et_3N/CH_2Cl_2$/DMAP,
or, if it is desired that: $PG^1$-$PG^2$=—$C(CH_3)_2$—, i.e. $X^1$=O-$PG^2$(-$PG^1$-), and Q=H:
  ii) TBAF/THF, (→$PG^1$=$PG^2$=Q=H)
  iii) $CH_2$=$C(CH_3)$—O—$CH_3$ or $(CH_3)_2C(OCH_3)_2$/TsOH
or, if it is desired that: $PG^1$-TMS and $X^1$=F:
Compounds 509 or 510 (e.g. prepared as in Scheme 1a) replace compounds 503 and 504 of Scheme 1;
or, if it is desired that: $PG^1$=TMS and $X^1$=F, Cl, Br, or I and Q=H:
  ii) TBAF/THF, (→$PG^1$=$PG^2$=Q=H, i.e. $X^1$=OH)
  iii) Conversion of $X^1$ (=OH) to $X^1$=F, Cl, Br, or I, for example as shown in Scheme 2;
  iv) optional conversion of $PG^1$=H to $PG^1$=H to $PG^1$=TMS, e.g. with $Me_3SiCl/Et_3N/CH_2Cl_2$/DMAP (c) i) II+BuLi; ii) 1; iii) optional alkylation of 22-OH with RZ/base (Z=Good leaving group, e.g. Hal, Ms, Ts, or Tf)
(d) Triplet sensitized photo-isomerization of the vitamin D triene, 5(6)(E) to 5(6)(Z); ii) optional alkylation of 22-OH with RZ/base
(e) i) Deprotection with $HF/CH_3CN/EtOAc$ or TBAF/THF, optionally followed by or preceded by PPTS/EtOH.

Scheme 1a

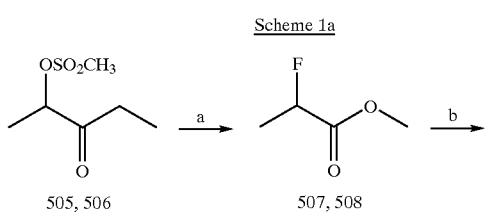

505, 506    507, 508

509, 510

Notes to Scheme 1a:
(a) KF, $HCONH_2$, 70° C. (method of Fritz-Langhals, E. et al, *Tetr. Lett.* 1993, 34, 293)
(b) $CH_3NH$—$OCH_3$, HCl, EtMgBr (3 eqv)

Compounds I can be prepared from the vitamin D-derived aldehyde compound 1, a synthesis of which has been reported (Calverley, M. J., *Tetrahedron*, 1987, 43, 4609.), for example by the routes outlined in Scheme 1, by reaction with an organometallic derivative of the side chain building blocks of general formula II.

The Compounds II to be used for making the Compounds I where X=OH can be synthesized as follows:

L(−)Ethyl lactate or D(+)ethyl lactate (or the corresponding methyl ester) is protected by silylation with tert-butyldimethylsilyl chloride to give the corresponding ethyl TBS-lactate (501, 502). This is converted, in a direct procedure with ethyl magnesium bromide, to the corresponding ethylketone, (503, 504), via the intermediary N-methoxy-N-methylamides, by the method of Williams, J. M. et al. (*Tetr. Lett.*, 1995, 36, 5461).

The ketone 503 or 504 is converted to the partially protected side chain synthon of general formula II by reaction with an organometallic reagent of the type Q-C≡C—$(CH_2)_n$-Met; (Met=-Li, -MgHal; -$AlBr_2$, -Hal+ e.g. $SmI_2$; Q=H or $Me_3Di$; n=1, 2 or 3). In the case of Q-C≡C—$(CH_2)_n$-Hal+e.g. $SmI_2$, a Barbier type reaction between a halide, a ketone, and a metal/metal salt is referred to.

A mixture of two diastereoisomers is usually formed: The R and the S isomer at the carbon atom marked (25) in Scheme 1, that is the carbon atom which ends up being the carbon atom C(25) in the final compound of formula I. If desired, the two diastereoisomers may be separated at this stage, or later during the synthesis of the side chain synthons II, if this is more convenient.

The following steps in the synthesis of the fully protected side chain synthons II are: 1) If Q is trimethylsilyl, Q is converted into hydrogen by deprotection, e.g. by means of a base. 2) The unprotected hydroxy group at the carbon marked (25) is protected, e.g. by silylation with TMS-Cl; such that $PG^1$=TMS (and $PG^2$=TBS).

Alternatively the TBS group ($PG^2$) of compound II may be removed, e.g. by TBAF (if Q=TMS, this is converted to H at the same time). The two hydroxy groups at the carbon atoms marked (25) and (26), respectively, can then be protected in one step, by conversion into a cyclic acetal or ketal, e.g. an acetonide (isopropylidene ketal), e.g. by means of e.g. 2-methoxypropene or 2,2-dimethoxypropane and an acid, such that $PG^1$ and $PG^2$ are connected into one group: —$C(CH_3)_2$—. Other methods of protection of 1,2-diols are described in the literature, e.g. in: Greene, T. W. and Wuts, P. G. M., "Protective Groups in Organic Synthesis", Sec. Ed., John Wiley and Sons, New York 1991, pp 118–142. An advantage of using cyclic acetals or ketals, such as acetonides, as protective groups of compounds II is that they are particularly well suited for establishing the stereochemistry at carbons (25) and (26) by way of Nuclear Overhauser Enhancement (NOE) NMR spectroscopy.

The Compounds II to be used for making the Compounds I where X=F may be synthesized from ketone 509 or 510, using the method of Scheme 1a and the intermediates of Table 1a:

TABLE 1a

Fluorinated Side Chain Building Blocks of Scheme 1a

| Prep | Comp | G.P. | C(26) |
|---|---|---|---|
| 42 | 505 | 11 | R |
| 43 | 506 | 11 | S |
| 44 | 507 | 12 | S |
| 45 | 508 | 12 | R |
| 46 | 509 | 1a | S |
| 47 | 510 | 1a | R |

The compounds II to be used for making the Compounds I where X is Cl, Br, or I are preferably made (and for X=F may be made) from the corresponding Compounds II where O-PG$^1$ and O-PG$^2$ (=X$^1$) are both OH, for example as shown in Scheme 2:

Scheme 2

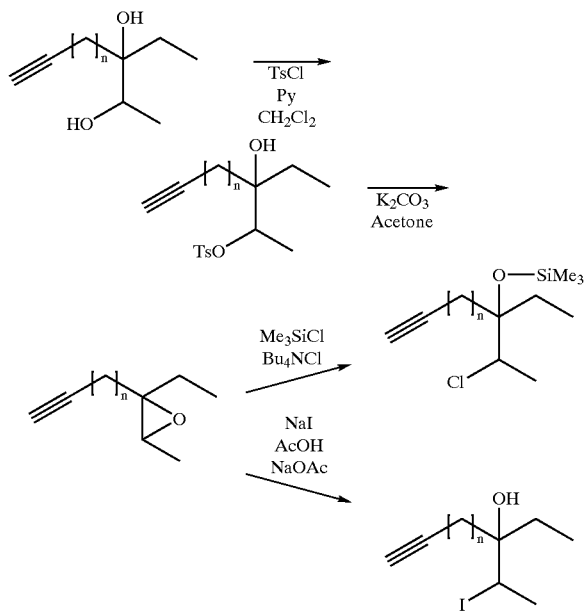

Note to Scheme 2

The compounds II where X$^1$=Cl or I can be converted to each other or converted to the corresponding compounds where X$^1$=F or Br by standard methods, e.g. as described in: R. C. Larock, *Comprehensive Organic Transformations*, VCH Publishers, Inc., New York, N.Y., USA, 1989, pp. 337–339 hereby incorporated by reference.

TABLE 2

Side Chain Building Blocks of General Formula II (Scheme 1)

| Prep | Comp | G.P. | Q | n | C(25) | C(26) | PG$^1$ | PG$^2$ |
|---|---|---|---|---|---|---|---|---|
| 4 | 201 | 2 | H | 1 | S | S | H | TBS |
| 5 | 202 | 4 | H | 1 | S | S | H | H |
| 6 | 203 | 5 | H | 1 | S | S | —C(CH$_3$)$_2$— | |
| 7 | 204 | 6 | H | 1 | S | S | TMS | TBS |
| 8 | 205 | 2 | H | 1 | R | S | H | TBS |
| 9 | 206 | 4 | H | 1 | R | S | H | H |
| 10 | 207 | 5 | H | 1 | R | S | —C(CH$_3$)$_2$— | |
| 11 | 208 | 6 | H | 1 | R | S | TMS | TBS |

TABLE 2-continued

Side Chain Building Blocks of General Formula II (Scheme 1)

| Prep | Comp | G.P. | Q | n | C(25) | C(26) | PG$^1$ | PG$^2$ |
|---|---|---|---|---|---|---|---|---|
| 12 | 209 | 2 | H | 1 | R | R | H | TBS |
| 13 | 210 | 6 | H | 1 | R | R | TMS | TBS |
| 14 | 211 | 2 | H | 1 | S | R | H | TBS |
| 15 | 212 | 6 | H | 1 | S | R | TMS | TBS |
| 16 | 213 | 3 | H | 0 | S | S | H | TBS |
| 17 | 214 | 3a | TMS | 0 | S | S | H | TBS |
| 18 | 215 | 4 | H | 0 | S | S | H | H |
| 19 | 216 | 5a | H | 0 | S | S | —C(CH$_3$)$_2$— | |
| 16 | 217 | 3 | H | 0 | R | S | H | TBS |
| 17 | 218 | 3a | TMS | 0 | R | S | H | TBS |
| 18 | 219 | 4 | H | 0 | R | S | H | H |
| 20 | 220 | 5a | H | 0 | R | S | —C(CH$_3$)$_2$— | |

Note to Table 2:
X$^1$ = O-PG$^2$

TABLE 2a

Fluorinated Side Chain Building Blocks of General Formula II (Scheme 1)

| Prep | Comp | G.P. | Q | n | C(25) | C(26) | PG$^1$ | X$^1$ |
|---|---|---|---|---|---|---|---|---|
| 48 | 221 | 2a | H | 1 | R/S | S | H | F |
| 49 | 222 | 6 | H | 1 | R/S | S | TMS | F |
| 50 | 223 | 2a | H | 1 | R/S | R | H | F |
| 51 | 224 | 6 | H | 1 | R/S | R | TMS | F |

The reaction of the aldehyde 1 with the organometallic reagents derived from the side chain building blocks II, can be performed by standard methods of nucleophilic addition of organometallic reagents to carbonyl compounds; i.e. by reacting the alkyne intermediate II with a Grignard reagent, such as ethyl magnesium bromide, or an alkyl lithium, such as butyl lithium (General Procedure 7) in a suitable anhydrous solvent, such as ether and/or THF, to generate the metal acetylide, then adding 1, to give III after usual aqueous work-up (which is normally implied in all the reactions of Scheme 1. In general the reaction product III is a mixture of the two possible C-22 epimers, here designated IIIA and IIIB. It is usually preferable to separate the IIIA and IIIB epimers which can conveniently be done by chromatography.

Nonlimiting illustrations of such compounds of formula III are given in Tables 3 and 3a. Compounds IIIA are formed in much higher yields than the corresponding IIIB epimers, typically in the ratio of about 95 to 5. Compounds IIIA, IVA and IA have 22(S) stereochemistry, and the corresponding compounds with the suffix B have 22(R) stereochemistry. Compounds IA are the preferred ones.

The optional alkylation of the 22-hydroxy compounds of general formula III or IV to yield the corresponding compound III or IV where R is (C$_1$–C$_6$)alkyl, phenyl, or (C$_7$–C$_9$) aralkyl can be performed by standard methods well known to the specialist. Illustrative, but non limiting, compounds of this sort are listed in Table 3.

In the alkylation reaction use is preferably made of an alkylating agent RZ, in which Z stands for a good leaving group, such as for example Hal, Ms, Tf; the RZ being allowed to react with the anion of the appropriate compound III or IV (R=H), derived therefrom by means of a suitable strong base, such as an alkali-metal alkoxide, alkyl alkali-metal or alkali-metal hydride. A suitable crown ether may be added as a phase transfer agent to accelerate the alkylation process. A useful method is described in General Procedure 9.

The photo-isomerization of the vitamin D triene, 5(6)(E), Compounds III of Scheme 1, to 5(6)(Z), Compounds IV of Scheme 1, is performed by means of UV-light in the presence of a triplet sensitizer, e.g. anthracene; useful methods are described in General Procedure 8 and and 8a. Nonlimiting illustrations of such compounds of general formula IV are given in Tables 3 and 3a, along with references to the preparation of each compound.

The triplet sensitized photo-isomerization of the vitamin D triene, 5(6)(E), Compounds III, to 5(6)(Z), Compounds IV, and the (optional) alkylation of the 22-OH-group with RHal/base, to form a 22-O—R compound where R≠H, may be performed in arbitrary order, according to what is most convenient in each case.

The final step in the synthesis of Compounds I of the present invention, examples of which are listed in Table 4, is one or more deprotection procedures to remove all protective groups of the compounds of general formula IV of Scheme 1. The deprotection may for example be performed either with TBAF to remove silyl groups, like TMS or TBS groups (General Procedure 4), or with HF which removes both silyl groups and acid sensitive protective groups, such as isopropylidene (ketal) groups (General Procedure 10). Alternatively, if both types of protective groups are to be removed, two different selective procedures may be used in sequence, e.g. as described in WO97/46522 (G.P. 7): The silyl groups are removed with TBAF, followed by the use of PPTS which selectively removes acid-sensitive protective groups; (or in the reverse order).

TABLE 3

Intermediates of General Formulas III and IV (Scheme 1)

| Type | Prep | Comp | G.P. | R | n | C(25) | C(26) | PG$^1$ | PG$^2$ |
|---|---|---|---|---|---|---|---|---|---|
| IIIA | 21 | 301 | 7 | H | 1 | S | S | TMS | TBS |
| IIIB | 21 | 302 | 7 | H | 1 | S | S | TMS | TBS |
| IVA | 22 | 401 | 8 | H | 1 | S | S | TMS | TBS |
| IVA | 23 | 402 | 9 | Me | 1 | S | S | TMS | TBS |
| IVA | 24 | 403 | 9 | Et | 1 | S | S | TMS | TBS |
| IVA | 25 | 404 | 9 | Pr | 1 | S | S | TMS | TBS |
| IVA | 26 | 405 | 9 | Bn | 1 | S | S | TMS | TBS |
| IIIA | 27 | 303 | 7 | H | 1 | R | S | TMS | TBS |
| IVA | 28 | 406 | 8 | H | 1 | R | S | TMS | TBS |
| IVA | 29 | 407 | 9 | Et | 1 | R | S | TMS | TBS |
| IIIA | 30 | 304 | 7 | H | 1 | R | R | TMS | TBS |
| IVA | 31 | 408 | 8 | H | 1 | R | R | TMS | TBS |
| IVA | 32 | 409 | 9 | Et | 1 | R | R | TMS | TBS |
| IIIA | 33 | 305 | 7 | H | 1 | S | R | TMS | TBS |
| IVA | 34 | 410 | 8 | H | 1 | S | R | TMS | TBS |
| IVA | 35 | 411 | 9 | Et | 1 | S | R | TMS | TBS |
| IIIA | 36 | 306 | 7a | H | 0 | S | S | —C(CH$_3$)$_2$— | |
| IVA | 37 | 412 | 8 | H | 0 | S | S | —C(CH$_3$)$_2$— | |
| IVA | 38 | 413 | 9 | Et | 0 | S | S | —C(CH$_3$)$_2$— | |
| IIIA | 39 | 307 | 7a | H | 0 | R | S | —C(CH$_3$)$_2$— | |
| IVA | 40 | 414 | 8 | H | 0 | R | S | —C(CH$_3$)$_2$— | |
| IVA | 41 | 415 | 9 | Et | 0 | R | S | —C(CH$_3$)$_2$— | |

Note to Table 2:
X$^1$ = O-PG$^2$

TABLE 3a

Fluorinated Intermediates of General Formulas III and IV (Scheme 1)

| Type | Prep | Comp | G.P. | R | n | C(25) | C(26) | PG$^1$ | X$^1$ |
|---|---|---|---|---|---|---|---|---|---|
| IIIA | 52 | 308 | 7 | H | 1 | R/S | S | TMS | F |
| IVA | 53 | 416 | 8a | H | 1 | R/S | S | TMS | F |
| IVA | 54 | 417 | 9 | Et | 1 | R/S | S | H | F |
| IIIA | 55 | 309 | 7 | H | 1 | R/S | R | TMS | F |
| IVA | 56 | 418 | 8a | H | 1 | R/S | R | TMS | F |
| IVA | 57 | 419 | 9 | Et | 1 | R/S | R | H | F |

Exemplified Compounds I of the invention are listed in Table 4, the numbered examples giving reference to illustrative methods of synthesis, together with spectroscopic data for the exemplified compounds.

The Compounds, 110, 112–113, 115 and 117–156 are made in a sequence of synthetic steps which is analogous to the sequence used for the preparations of Compounds, 101–109, 111, 114, 116 and 157–160, Examples 1–12 and 16–19:

Compound 1 and the appropriate side chain building blocks of General Formula II, H—C≡C—(CH$_2$)$_n$—C(C$_2$H$_5$)(OPG$^1$)-CH(X$^1$)CH$_3$, are reacted, according to General Procedure 7 (G.P. 7), to give the corresponding compound of formula III.

If not mentioned in Tables 2 or 2a, the compounds II in question can be prepared by similar methods to those applied for the synthesis of the compounds II listed in Tables 2 or 2a.

The compound of formula III is photoisomerized, according to G.P. 8 or 8a, to give the corresponding compound of formula IV.

Optionally, the compound of formula IV and the appropriate alkylating agent RZ are reacted, according to G.P. 9, to give the corresponding compound of formula IV where R≠H. The photoisomerization step and alkylation step may be performed in the reverse order, if desired.

As the last step, the compound of formula IV is deprotected, according to either G.P. 4 or G.P. 10 to give the Compound I in question.

TABLE 4

Compounds of General Formula I

| Type | Exam | Comp | G.P. | R | n | X | C(25) | C(26) |
|---|---|---|---|---|---|---|---|---|
| IA | 1 | 101 | 4 | H | 1 | OH | S | S |
| IA | 2 | 102 | 4 | Me | 1 | CH | S | S |
| IA | 3 | 103 | 4 | Et | 1 | OH | S | S |
| IA | 4 | 104 | 4 | Pr | 1 | OH | S | S |
| IA | 5 | 105 | 4 | Bn | 1 | OH | S | S |
| IA | 6 | 106 | 4 | Et | 1 | OH | R | S |
| IA | 7 | 107 | 4 | Et | 1 | OH | R | R |
| IA | 8 | 108 | 4 | Et | 1 | OH | S | R |
| IA | 9 | 109 | 10 | H | 0 | OH | S | S |
| IA | | 110 | 10 | Me | 0 | OH | S | S |
| IA | 10 | 111 | 10 | Et | 0 | OH | S | S |
| IA | | 112 | 10 | Pr | 0 | OH | S | S |
| IA | | 113 | 10 | Bn | 0 | OH | S | S |
| IA | 11 | 114 | 10 | H | 0 | OH | R | S |
| IA | | 115 | 10 | Me | 0 | OH | R | S |
| IA | 12 | 116 | 10 | Et | 0 | OH | R | S |
| IA | | 117 | 10 | Pr | 0 | OH | R | S |
| IA | | 118 | 10 | H | 0 | OH | R | R |
| IA | | 119 | 10 | Et | 0 | OH | R | R |
| IA | | 120 | 10 | H | 0 | OH | S | R |
| IA | | 121 | 10 | Me | 0 | OH | S | R |
| IA | | 122 | 10 | Et | 0 | OH | S | R |
| IA | | 123 | 10 | Pr | 0 | OH | S | R |
| IA | | 124 | 10 | H | 1 | OH | R | R |
| IA | | 125 | 10 | Me | 1 | OH | R | S |
| IA | | 124 | 10 | H | 1 | OH | R | R |

TABLE 4-continued

Compounds of General Formula I

| Type | Exam | Comp | G.P. | R  | n | X  | C(25) | C(26) |
|------|------|------|------|----|---|----|-------|-------|
| IA   |      | 125  | 10   | Me | 1 | OH | R     | R     |
| IA   |      | 126  | 10   | H  | 1 | OH | S     | R     |
| IA   |      | 127  | 10   | Me | 1 | OH | S     | R     |
| IA   |      | 128  | 10   | Pr | 1 | OH | S     | R     |
| IA   |      | 129  | 10   | Bn | 1 | OH | S     | R     |
| 1A   |      | 131  | 10   | H  | 2 | OH | S     | S     |
| IA   |      | 132  | 10   | Me | 2 | OH | S     | S     |
| IA   |      | 133  | 10   | Et | 2 | OH | S     | S     |
| IA   |      | 134  | 10   | Pr | 2 | OH | S     | S     |
| IA   |      | 135  | 10   | Bn | 2 | OH | S     | S     |
| IA   |      | 136  | 10   | Et | 2 | OH | R     | S     |
| IA   |      | 137  | 10   | Et | 2 | OH | R     | R     |
| IA   |      | 138  | 10   | H  | 2 | OH | S     | R     |
| IA   |      | 139  | 10   | Me | 2 | OH | S     | R     |
| IA   |      | 140  | 10   | Et | 2 | OH | S     | R     |
| IA   |      | 141  | 10   | Pr | 2 | OH | S     | R     |
| IB   |      | 142  | 10   | Et | 1 | OH | S     | S     |
| IA   |      | 143  | 10   | Me | 0 | F  | S     | S     |
| IA   |      | 144  | 10   | Me | 0 | F  | S     | R     |
| IA   |      | 145  | 10   | Et | 0 | F  | S     | S     |
| IA   |      | 146  | 10   | Et | 0 | F  | S     | R     |
| IA   |      | 147  | 10   | Me | 1 | F  | S     | S     |
| IA   |      | 148  | 10   | Me | 1 | F  | S     | R     |
| IA   |      | 149  | 10   | Et | 1 | F  | S     | S     |
| IA   |      | 150  | 10   | Et | 1 | F  | S     | R     |
| IA   |      | 151  | 10   | Et | 2 | F  | S     | S     |
| IA   |      | 152  | 10   | Me | 0 | Cl | S     | S     |
| IA   |      | 153  | 10   | Et | 0 | Cl | S     | S     |
| IA   |      | 154  | 10   | Me | 1 | Cl | S     | S     |
| IA   |      | 155  | 10   | Et | 1 | Cl | S     | S     |
| IA   |      | 156  | 10   | Et | 1 | Cl | S     | R     |
| IA   | 16   | 157  | 10   | H  | 1 | F  | R/S   | S     |
| IA   | 17   | 158  | 10   | Et | 1 | F  | R/S   | S     |
| IA   | 18   | 159  | 10   | H  | 1 | F  | R/S   | R     |
| IA   | 19   | 160  | 10   | Et | 1 | F  | R/S   | R     |

The present compounds are intended for use in pharmaceutical compositions which are useful in the local or systemic treatment or prophylaxis of human and veterinary disorders, such as e.g. psoriasis (including pustulosis palmoplantaris, acrodermatitis continua and nail psoriasis) and other disturbances of keratinization, HIV-associated dermatoses, wound healing, various cancer forms, such as leukemia, mammary cancer, brain glial tumours, osteosarcoma, myelofibrosis, melanoma, other skin cancers, and of diseases of, or imbalances in, the immune system, such as host versus graft and graft versus host reaction and transplant rejection, and autoimmune diseases, such as discoid and systemic lupus erythematosus, diabetes mellitus and chronic dermatoses of auto-immune type, e.g. scleroderma and pemphigus vulgaris, and inflammatory diseases, such as asthma and rheumatoid arthritis, as well as a number of other diseases states including hyperparathyroidism, particularly secondary hyperparathyroidism associated with renal failure, cognituve impairment or senile dementia (Alzheimers disease) and other neurodegenerative diseases, hypertension, acne, alopecia, skin atrophy, e.g. steroid induced skin atrophy, skin ageing, including photo-ageing, and to their use for promoting osteogenesis and treating/preventing osteoporosis and osteomalacia.

The present compounds may be used in combination with other pharmaceuticals or treatment modalities. In the treatment of psoriasis the present compounds may be used in combination with other antipsoriatic drugs, e.g steroids, or with other treatments e.g. light- or UV-light-treatment or the combined PUVA-treatment. In the treatment of cancer the present compounds may be used in combination with other anti-cancer drugs or anti-cancer treatments, such as radiation treatment. In the prevention of graft rejection and graft versus host reaction, or in the treatment of auto-immune diseases, the present compounds may advantageously be used in combination with other immunosuppressive/immunoregulating drugs or treatments, e.g. with cyclosporin A.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

The formulations, both for veterinary and for human medical use, of the present invention thus comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, ophthalmic, rectal, parenteral (including subcutaneous, intramuscular and intravenous), transdermal, intra-articular and topical, nasal or buccal administration.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient which is preferably isotonic with the blood of the recipient. Transdermal formulations may be in the form of a plaster.

Formulations suitable for intra-articular or ophthalmic administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers.

In addition to the aforementioned ingredients, the formulations of this invention may include one or more additional ingredients, such as diluents, binders, preservatives etc.

The compositions may further contain other therapeutically active compounds usually applied in the treatment of the above mentioned pathological conditions, such as other immunosuppressants in the treatment of immunological diseases, or steroids in the treatment of dermatological diseases.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the systemic treatment daily doses from 0.001–2 μg per kilogram body weight, preferably from 0.002–0.3 μg/kg of mammal body weight, for example 0.003–0.2 μg/kg of a compound of formula I are administered, typically corresponding to a daily dose for an adult human of from 0.2 to 15 μg. In the topical treatment of dermatological disorders, ointments, creams or lotions containing from 0.1–500 μg/g, and preferably from 0.1–100 μg/g, of a compound of formula I are administered. For topical use in ophthalmology ointments, drops or gels containing from 0.1–500 μg/g, and preferably from 0.1–100 μg/g, of a compound of formula I are administered. The oral compositions are formulated, preferably as tablets, capsules, or drops, containing from 0.05–50 μg, preferably from 0.1–25 μg, of a compound of formula I, per dosage unit.

The invention is further illustrated by the following General Procedures, Preparations and Examples:

EXAMPLES

General Procedures, Preparations and Examples
General:

THF was dried over 4A molecular sieves. Reactions were routinely run under an argon atmosphere unless otherwise noted. In the standard work-up procedure, the reaction mixture was poured into water and extracted three times with a suitable organic solvent. The organic layer was washed with water and saturated sodium chloride solution, dried over anhydrous sodium sulfate, and concentrated in vacuo to give the product, which was purified by chromatography on silica gel (40–63 μm), by crystallisation, or by distillation.

For $^1$H nuclear magnetic resonance spectra (300 MHz) and $^{13}$C NMR (75.6 MHz) chemical shift values ($\delta$) (in ppm) are quoted, for deuteriochloroform solutions, except where noted, relative to internal tetramethysilane ($\delta$=0.00) or chloroform ($\delta$=7.25) or deuteriochloroform ($\delta$=76.81 for $^{13}$C NMR). The value for a multiplet, either defined (doublet (d), triplet (t), quartet (q)) or not (m) at the approximate midpoint is given unless a range is quoted (s=singlet, b=broad).

General Procedures

General Procedure 1

Synthesis of Ketones and 503 and 504

To a solution/suspension of the appropriate silylated ethyl lactate, compound 501 or 502, (23.2 g, 0.1 mol) and N,O-dimethyl hydroxyl amine hydrochloride (12.2 g, 0.125 mol) in dry THF (800 ml) was added a 3.0 molar solution of ethyl magnesium bromide in ether (167 ml, 0.5 mol), during one hour, while stirring and cooling to −5° C. Stirring was continued for 18 hours at 25° C., after which the reaction mixture was hydrolyzed by pouring it into a solution of ammonium chloride (160 g) in water (1.2 l). After work up with ether, the crude product was purified by chromatography (eluant: 0% to 1% ether in petroleum ether) to give the desired compound.

Variation:

General Procedure 1a

Synthesis of Ketones 509 and 510

To a solution/suspension of the appropriate R or S, methyl or ethyl, 2-fluoropropionate (0.1 mol) and N,O-dimethylhydroxylamine hydrochloride (10.7 g, 0.11 mol) in dry THF (300 ml) was added a 3.0 molar solution of ethylmagnesium bromide in ether (107 ml, 0.32 mol), during one hour, while stirring and cooling to 0 to −5° C. Stirring was continued for 4 hours at 0° C. and 16 hours at 25° C., after which the reaction mixture was hydrolyzed by addition of 25% aqueous ammonium chloride (300 ml) with vigorous stirring. The temperature rose to about 35° C. and was kept there by means of a hot water bath; the pH was monitored with a pH-meter (pH about 8). After 15 minutes the pH was adjusted to 3 with 4N aqueous hydrochloric acid and stirring was continued for 15 minutes. The resulting two-phase mixture was separated and the aqueous phase was extracted twice with ether (50 ml). The combined organic phases were extracted twice with saturated sodium chloride solution (25 ml) and dried over anhydrous sodium sulfate. The solution of crude material was concentrated by distilling off the ether and some of the THF at atmospheric pressure through an an efficient still ($\frac{1}{16}$" Dixon gauze rings packed in a 7 cm column). The residue (about 200 g) was fractionated through a 15 cm Vigreux-column connected to a dry-ice cooled condenser and receiver. By gradually lowering the pressure to 0.25 bar fractions consisting of THF and an increasing part of the title compound were collected (leaving a residue of higher boiling intermediate- and side-products). If desired, the first fractions may be concentrated by redestillation. The pure title compounds have a b.p. of about 45° C./27 mbar; fractions mixed with THF were, however, usable in the next synthetic step, when dried and the percentage of title compound determined by NMR.

General Procedure 2

Synthesis of Tertiary Propargylic Alcohols, Compounds II

A mixture of aluminium scales (0.45 g), mercury(II) chloride (12 mg) and dry THF (10 ml) was stirred for 20 minutes. A solution of propargyl bromide (1.88 ml, 2.97 g, 25 mmol) in dry THF (5 ml) was added, with stirring, during 20 minutes, at 25°–30° C. Stirring was continued for 30 minutes at 40° C. A solution of the appropriate ketone, Compound 503 or 504, (5.0 g, 23 mmol) in dry THF (10 ml) was added, during 10 minutes, at 25° C.; the reaction mixture was stirred for a further 1½ hours at 25° C. and then worked up with ether. The crude product was purified by chromatography, with 1% ether in petroleum ether as eluant, which procedure was repeated twice, with suitable combination of fractions, to give each of the two isomeric title compounds in a pure state.
Variation:

General Procedure 2a

Synthesis of Fluorinated Tertiary Propargylic Alcohols, Compounds II

A 1.5 M solution of allenylmagnesium bromide in ether (13 ml, about 20 mmol) (L. Brandsma, "Preparative Acetylenic Chemistry", $2^{nd}$ Ed., Elsevier, Amsterdam 1988, pp. 35–36) was cooled to −40° C., and a dry solution of the ketone 509 or 510 (16 mmol) in THF (20 ml) was added with stirring, during 30 minutes, followed by stirring for 10 minutes, while cooling to −30° C.—−40° C. The reaction mixture was poured into 25% aqueous ammonium chloride (50 ml), while stirring and cooling in ice. The aqueous phase was extracted with ether (20 ml) and the combined organic phases were dried with magnesium sulfate and concentrated in vacuo to give the title compound as an oil. This product consisted of the two epimers in a ratio of about 3:1 and was used in the next synthetic step without further purification.

General Procedure 3

Synthesis of Tertiary Acetylenic Alcohols, Compounds II

To a stirred suspension of lithium acetylide, ethylenediamine complex (5.3 g, 58 mmol) in dry THF (250 ml) was added a solution of the appropriate ketone, Compound 503 or 504, (12.5 g, 58 mmol) in dry THF (50 ml), during 20 minutes, at 35° C. Stirring was continued for 4 hors at 25° C., after which the reaction mixture was hydrolyzed by pouring it into a solution of sodium chloride (780 g) in water (200 ml). After work up with ether, the crude product was purified by chromatography (eluant: 0% to 2% ether in petroleum ether) to give the two isomeric title compounds as an only partially separable, but otherwise pure, mixture. This mixture was used as such in the next step, the removal of the silyl protection group, after which the two isomeric 25, 26-diols could be separated by means of chromatography.

General Procedure 3a

Synthesis of Tertiary Trimethylsilyl Acetylenic Alcohols, Compounds II

To a stirred solution of trimethylsilylacetylene (0.25 ml, 0.177 g, 1.8 mmol) in dry THF (6 ml) was added a 1.6 molar solution of butyl lithium in hexane (0.83 ml, 1.3 mmol), during 10 minutes, at −60° C. Stirring was continued for 10 minutes at −60° C. and at 25° C. for 30 minutes. The resulting solution of lithium trimethylsilylacetylide was again cooled to −60° C. and a solution of the appropriate ketone, Compound 503 or 504, (0.3 g, 1.4 mmol) in dry THF (1 ml), was added during 2 minutes. Stirring was continued for 3 hours at −60° C., after which the reaction mixture was hydrolyzed by pouring it into a solution of ammonium chloride (2 g) in water (20 ml). After work up with ether, the crude product was purified by chromatography (eluant: 0% to 1% ether in petroleum ether) to give the two isomeric title compounds as an inseparable mixture. This was used as such in the next step, the removal of both silyl protection groups, after which the two isomeric 25,26-diols could be separated by means of chromatography.

General Procedure 4

Deprotection of Silyl-Protected Compounds with TBAF

To a solution of the appropriate mono-silyl protected compound(s) (0.4 mmol), or di-silyl protected compound(s) (0.2 mmol), or tetra-silyl protected compound(s) (0.1 mmol) in THF (10 ml) was added TBAF trihydrate (0.32 g, 1.0 mmol), (i.e. 2.5 mol of TBAF for each molar equivalent of silyl protection group), and the mixture was heated to reflux for one hour with stirring. After addition of 1M sodium hydrogen carbonate (10 ml), the mixture was worked up with ether or ethyl acetate. The residue was purified by chromatography to yield the desired compound(s).

General Procedure 5

Protection of 25,26-Diols II as Acetonides, Using 2-Methoxypropene

A solution of an unprotected 25,26-diol, Compound II, (0.35 mmol), 2-methoxypropene (50 mg, 0.7 mmol) and p-toluenesulfonic acid (1 mg) in dry DMF (2 ml), containing 3 Å molecular sieves (1/16" rods, about 0.1 g) was heated to 70° C., with stirring, for 30° minutes. After work up with ether, the crude product was purified by chromatography with 5% ether in petroleum ether as eluant to give the pure acetonide, Compound II.

General Procedure 5a

Protection of 25,26-Diols II as Acetonides, Using 2,2-Dimethoxypropane

A solution of an unprotected 25,26-diol, Compound II, (2.0 mmol), 2,2-dimethoxy-propane (2 ml, 1.7 g, 16 mmol) and p-toluene sulfonic acid (38 mg) in dry acetone (10 ml) was stirred at 25° C. 2 hours. Triethylamine (1 ml) was added and the reaction mixture was concentrated to about 2 ml, using a short (about 3 cm) Vigreux column, at about b.p. 30° C./0.4 bar. Water (2 ml) and 1M sodium hydrogen carbonate (1 ml) were added, and the mixture was extracted with ether (3×8 ml). The combined ether extracts were dried with magnesium sulfate, and concentrated to about 0.5 ml (as above). The crude product was purified by chromatography with 5% ether in petroleum ether as eluant. After concentration (as above) of the appropriate combined fractions the pure acetonide, Compound II, was obtained.

General Procedure 6

Protection of 25-Monohydroxy Compounds II by Trimethylsilylation

Trimethylchlorosilane (1.08 g, 10 mmol) was added during 10 minutes, at 0° C., to a stirred solution of a 25-hydroxy-26-tert-butyldimethylsilyloxy- (or 26-fluoro-) compound II (5.0 mmol), triethylamine (1.51 g, 15 mmol) and DMAP (5 mg) in dry dichloromethane (10 ml). Stirring was continued for 48 hours at 25° C. After work up (with ether) the crude product was purified by chromatography with petroleum ether as eluant to give the pure 25-trimethylsilyloxy-26-tert-butyldimethylsilyloxy- (or 26-fluoro-) compound II.

General Procedure 7

Synthesis of Compounds III from Compound 1 and Side Chain Building Block II

To a solution of the appropriate side chain building block, Compound II, (3.0 mmol) in dry HF (5 ml), cooled to −78° C. and stirred under argon, was added dropwise, during 2 minutes, a solution of n-butyl lithium (1.6 M in hexane; 1.5 ml). Stirring was continued at −78° C. for 15 minutes and at 20° C. for another 15 minutes. The mixture was again cooled to −78° C., and a solution of the aldehyde, compound 1, (1.5 mmol) in dry THF (5 ml) was added dropwise during 4 minutes; after that stirring was continued at −78° C. for 30 minutes. The reaction mixture was worked up (ether) to yield a crude product containing the isomeric 22-hydroxy compounds A (less polar) and B (more polar). These were separated by chromatography (mixture of ethyl acetate and petroleum ether as eluant) to yield the pure compounds III. Variation:

General Procedure 7a

The procedure of G.P. 7 was followed, except that 1.87 ml of n-butyl lithium (1.6M) and 3 mmol of compound 1 was used.

General Procedure 8

Photoisomerisation of Compound III to Compound IV

A solution of the appropriate compound III (0.28 mmol), anthracene (0.1 g) and triethylamine (0.20 ml, 1.4 mmol) in dichloromethane (16 ml) in a 25 ml round-bottomed Pyrex flask was irradiated at about 10° C. with UV-light from a high pressure ultraviolet lamp, type TQ760Z2 (Hanau), at 700 W, for 30 minutes (15 minutes at 0.08 mmol scale) while stirring. The reaction mixture was evaporated in vacuo, and the residue was treated with petroleum ether (2×2 ml) and filtered. The filtrate was concentrated and purified by chromatography to afford the desired compound IV.
Variation:

General Procedure 8a

A solution of the appropriate compound III (0.13 mmol), 9-acetylanthracene (23 mg) and triethylamine (0.10 ml, 0.7 mmol) in toluene (5 ml) in a 10 ml round-bottomed Pyrex tube was irradiated at about 10° C. with UV-light from a high pressure ultraviolet lamp, type TQ150Z2 (Hanau) (150 W) for 60 minutes. The reaction mixture was cooled to −20° C. and filtered. The filtrate was evaporated in vacuo, and the residue was purified by chromatography to afford the desired compound IV, together with some 9-acetyl-anthracene which was removed after the final (deprotection) step.

General Procedure 9

Alkylation of C-22-Hydroxy-Compound III or IV

To a solution of the appropriate 22-hydroxy compound (R=H) (0.5 mmol) in dry THF (5 ml) was added, while stirring at 20° C. under argon, a 20% suspension of potassium hydride in mineral oil (0.2 ml) followed by an alkylating agent, RZ (1.5 mmol) and, finally, during 5 minutes, a solution of 18-Crown-6 (0.13 g) in dry THF (2 ml). Stirring at 25° C. was continued for two hours, after which the reaction mixture was worked up (ether). The crude product was purified by chromatography (mixture of ether and petroleum ether as eluant) to yield the desired alkoxy compound III or IV.

General Procedure 10

Synthesis of Compound I by Deprotection of Compound IV with HF

To a stirred solution of the appropriate Compound IV (0.25 mmol) in ethyl acetate (3 ml) was added acetonitrile (6 ml) followed by a 5% solution of hydrofluoric acid in acetonitrile-$H_2O$ 7:1 (4 ml). After stirring for 2 hours at 25° C. ethyl acetate (40 ml) and 1M sodium hydrogen carbonate (20 ml) was added, and the reaction mixture was worked up (ethyl acetate). The residue was purified by chromatography to give the desired compound I.

General Procedure 11

Synthesis of Lactic Ester Mesylates

A solution of methanesulfonyl chloride (18.6 ml; 27.5 g; 0.24 mol) in tert-butyl methyl ether (100 ml) was added during one hour to a stirred solution of the appropriate R or S, methyl or ethyl, lactate (0.20 mol), triethylamine (28.3 g; 0.28 mol) and DMAP (0.24 g; 0.002 mol) in tert-butyl methyl ether (200 ml), while cooling in an ice bath. Stirring was continued for ½ hour in the ice bath a followed by 2 hours at 25° C. The reaction mixture was again cooled in an ice bath, and water (250 ml) was added slowly, keeping the temperature below 10° C. After stirring for 20 minutes more, the phases were separated, and the aqueous phase was extracted twice with ether (100 ml). The combined organic phases were extracted with: 1 N sulfuric acid (100 ml), water (100 ml), 1 M sodium hydrogen carbonate (100 ml), water (2×100 ml) and saturated aqueous sodium chloride (100 ml). After drying with sodium sulfate the solution was concentrated (at 35° C. and 0.2 bar), and the residue fractionated in vacuo through a 45 cm Podbielniak-type column to give the desired title compound.

General Procedure 12

Synthesis of R or S, Methyl or Ethyl, 2-Fluoropropionate

A solution of the appropriate lactic ester mesylate (0.125 mol) was added, during about one hour, to a solution/suspension of (freeze-dried) potassium fluoride (29 g; 0.5 mol) in formamide (70 ml) which was stirred and heated in an oil bath at 60° C., in a vacuum of about 27 mbar. The flask was equipped with a Claisen-type side arm which was connected to a dry-ice cooled and a dry-ice cooled receiver, in which was condensed the 2-fluoropropionic acid ester that was destilled continuously from the reaction. Stirring at 60° C. and 20 mm Hg was continued until no more distillate was condensed, this took 4–5 hours. The distillate (which contained some water) was diluted with ether (40 ml), dried with magnesium sulfate and purified by distillation in a setup similar to the one used for the above preparation, keeping the bath temperature fairly constant at 50–60° C. and gradually lowering the pressure, until the pure title compound was collected in the receiver.

Preparation 1
Compound 502

A solution of (+)-ethyl D-lactate (R-isomer, unnatural) (5.2 g, 44 mmol), imidazole (13.6 g) and tert-butyl dimethylsilylchloride (15 g) in dry DMF (50 ml) was stirred at 25° C. for 1 hour. Ethyl acetate (200 ml) was added and the organic solution was extracted with water (2×100 ml), 3M $CaCl_2$ (2×100 ml), water (100 ml) and 35% NaCl (100 ml), dried with sodium sulfate and concentrated in vacuo. The crude product was purified by chromatography with 1% ether in petroleum ether as eluant to give Compound 502 as an oil.
$[\alpha]_D^{20}$ +30.5° (c 2.14, $CHCl_3$)
$^{13}C$ NMR δ 173.9, 68.3, 60.5, 25.5, 21.1, 18.1, 14.0, −5.1, −5.5

Preparation 2
Compound 503
Method: General Procedure 1
Staring material: Ethyl (S)-(−)-O-tert-butyldimethylsilyllactate (Compound 501)
Chromatography eluant: 0% to 5% ether in petroleum ether
$[\alpha]_D^{20}$ −10.8° (c 2.17, $CHCl_3$)
$^{13}C$ NMR δ 214.7, 74.6, 29.9, 25.5, 20.8, 17.8, 7.1, −4.9, −5.3

Preparation 3
Compound 504
Method: General Procedure 1
Starting material: Compound 502
Chromatography eluant: 0% to 5% ether in petroleum ether.
$^{13}C$ NMR δ 214.7, 74.6, 29.9, 25.5, 20.8, 17.8, 7.1, −4.9, −5.3

Preparation 4
Compound 201(+Compound 205)
Method: General Procedure 2
Starting material; Compound 503
Chromatography eluant: 1% ether in petroleum ether.
$^{13}C$ NMR δ $^1H$ NMR d 81.1, 75.6, 71.3, 70.0, 26.5, 25.8, 25.6, 17.8, 17.1, 7.4 −4.3, −5.2

Preparation 5
Compound 202
Method: General Procedure 4
Starting material: Compound 201
Chromatography eluant: 25% to 50% ether in petroleum ether.
$^{13}C$ NMR δ 80.7, 75.5, 71.2, 71.1, 27.1, 26.0, 17.1, 7.6

Preparation 6
Compound 203
Method: General Procedure 5
Starting material: Compound 202
Chromatography eluant: 5% ether in petroleum ether.
$^{13}C$ NMR δ 106.8, 82.4, 80.2, 78.2, 70.8, 28.3, 26.7, 25.6, 25.0, 14.6, 7.2

Preparation 7
Compound 204
Method: General Procedure 6
Starting material: Compound 201
Chromatography eluant: petroleum ether.
$[\alpha]_D^{20}$ −4.4° (c 1.8, $CHCl_3$)
$^{13}C$ NMR δ 82.2, 80.1, 71.4, 70.3, 28.8, 25.8, 24.9, 17.9, 17.3, 7.5, 2.4, −4.4, −4.9

Preparation 8
Compound 205 (+Compound 201)
Method: General Procedure 2
Starting material: Compound 503
Chromatography eluant: 1% ether in petroleum ether.
$^{13}C$ NMR δ 80.8, 75.1, 72.3, 70.2, 27.8, 25.6, 24.4, 17.8, 17.6, 7.4, −4.3, −5.2

Preparation 9
Compound 206
Method: General Procedure 4
Starting material: Compound 205
Chromatography eluant: 25 to 50% ether in petroleum ether.
$^{13}C$ NMR δ 80.8, 75.2, 71.6, 71.1, 29.1, 24.7, 17.0, 7.4

Preparation 10
Compound 207
Method: General Procedure 5
Starting material: Compound 206
Chromatography eluant: 5% ether in petroleum ether.
$^{13}C$ NMR δ 106.9, 83.1, 81.0, 76.8, 70.1, 28.4, 28.2, 26.5, 24.5, 14.5, 8.1

Preparation 11
Compound 208
Method: General Procedure 6
Starting material: Compound 205
Chromatography eluant: petroleum ether.
$[\alpha]_D^{20}$ +6.9° (c 1.6, $CHCl_3$)
$^{13}C$ NMR δ 82.0, 79.8, 72.7, 70.5, 27.9, 27.0, 25.8, 25.7, 17.6, 8.3, 2.5, −4.4, −5.0

Preparation 12
Compound 209 (+Compound 211)
Method: General Procedure 2
Starting material: Compound 504
Chromatography eluant: 1–2% ether in petroleum ether.
$^{13}C$ NMR δ 81.1, 75.6, 71.3, 70.0, 26.5, 25.8, 25.6, 17.8, 17.1, 7.4, −4.3, −5.2

Preparation 13
Compound 210
Method: General Procedure 6
Starting material: Compound 209
Chromatography eluant: petroleum ether.
$[\alpha]_D^{20}$ +4.1° (c 2.1, $CHCl_3$)
$^{13}C$ NMR δ 82.2, 80.1, 71.4, 70.3, 28.8, 25.8, 25.0, 17.9, 17.3, 7.5, 2.4, −4.4, −4.9

Preparation 14
Compound 211 (+Compound 209)
Method: General Procedure 2
Starting material: Compound 504
Chromatography eluant: 1% to 2% ether in petroleum ether.
$^{13}C$ NMR δ 80.8, 75.1, 72.3, 70.2, 27.8, 25.6, 24.4, 17.8, 17.6, 7.4, −4.3, −5.2

Preparation 15
Compound 212
Method: General Procedure 6
Starting material: Compound 211
Chromatography eluant: petroleum ether.
$[\alpha]_D^{20}$ −7.0° (c 1.2, $CHCl_3$)
$^{13}C$ NMR δ 82.0, 79.8, 72.8, 70.5, 27.9, 27.0, 25.7, 17.8, 17.6, 8.3, 2.5, −4.4, −5.0

Preparation 16
Compound 213+Compound 217
Method: General Procedure 3
Starting material: Compound 503
Chromatography eluant: 0% to 2% ether in petroleum ether.
Compound 213
$^1H$ NMR δ 3.70 (q,1H), 2.51 (s,1H), 1.80 (m,1H), 1.64 (m,1H), 1.25 (d,3H), 0.98 (t,3H), 0.88 (s,9H), 0.20 (s,6H)
Compound 217
$^{13}C$ NMR δ 83.9, 74.7, 73.3, 73.1, 31.0, 25.6, 25.5, 18.6, 8.1, −4.3, −5.1

Preparation 17
Compound 214+Compound 218
Method: General Procedure 3a
Starting material: Compound 503
Chromatography eluant: 0% to 1% ether in petroleum ether.

Compound 214
$^{13}$C NMR δ 105.9, 89.2, 74.6, 73.5, 30.9, 25.7, 18.7, 17.2, 8.3, −0.3, −4.5, −4.9
Compound 218
$^{13}$C NMR δ 105.9, 89.6, 75.1, 73.4, 30.9, 25.7, 25.6, 18.7, 8.3, −0.3, −4.2, −5.0
Preparation 18
Compound 215+Compound 219
Method: General Procedure 4
Starting material: Compound 213+Compound 217 or Compound 214+Compound 218
Chromatography eluant: a) 40% ether in petroleum ether, b) 33% ether in petroleum ether
Compound 215
$^1$H NMR δ 3.84 (1H,q), 2.49 (1H,s), 1.74 (1H,m), 1.61 (1H,m), 1.27 (3H,d), 1.09 (3H,t)
Compound 219
Crystallised from ether/n-heptane, m.p. 52°–53°.
$^1$H NMR δ 3.65 (q,1H), 2.46 (s,1H), 1.65 (m,2H), 1.31 (d,3H), 1.08 (t,3H)
Preparation 19
Compound 216
Method: General Procedure 5a
Starting material: Compound 219
Chromatography eluant: 5% ether in petroleum ether.
$^{13}$C NMR δ 108.6, 83.9, 79.3, 79.2, 72.8, 29.3, 28.3, 26.0, 13.6, 8.2
Preparation 20
Compound 220
Method: General Procedure 5a
Starting material: Compound 215
Chromatography eluant: 5% ether in petroleum ether.
$^{13}$C NMR δ 108.6, 82.8, 81.3, 78.4, 75.1, 31.3, 27.6, 27.1, 15.8, 8.8
Preparation 21
Compound 301+Compound 302
Method: General Procedure 7
Starting material: Compound 204
Chromatography eluant: 0% to 10% ether in petroleum ether.
Compound 301
$^{13}$C NMR δ 153.4, 142.8, 135.3, 121.5, 116.4, 106.5, 83.2, 82.9, 80.3, 71.6, 70.1, 67.0, 64.6, 56.0, 51.4, 45.5, 43.8, 41.0, 39.6, 36.4, 29.0, 28.7, 26.4, 25.8, 25.7, 25.6, 25.2, 23.2, 21.9, 18.1, 17.9, 17.9, 17.3, 13.0, 12.4, 7.6, 2.5, −4.3, −5.0, −5.1
Compound 302
$^{13}$C NMR δ 152.5, 141.9, 134.3, 120.5, 115.4, 105.5, 82.3, 82.0, 79.3, 70.7, 69.1, 66.0, 64.7, 55.1, 51.1, 44.6, 42.8, 41.5, 39.2, 35.5, 28.0, 27.7, 26.0, 24.9, 24.7, 24.6, 24.4, 22.3, 21.0, 17.1, 17.0, 16.9, 16.4, 12.4, 10.8, 6.6, 1.5, −5.3, −5.8, −5.9
Preparation 22
Compound 401
Method: General Procedure 8
Starting material: Compound 301
Chromatography eluant: 0% to 2% ether in petroleum ether.
$^{13}$C NMR δ 148.2, 140.4, 135.0, 122.9, 117.9, 111.0, 83.1, 82.9, 80.3, 71.8, 71.6, 67.3, 64.6, 55.9, 51.4, 45.8, 45.3, 44.6, 41.0, 39.7, 29.0, 28.6, 26.5, 25.8, 25.7, 25.6, 25.2, 23.2, 21.8, 18.0, 17.9, 17.3, 13.0, 12.3, 7.6, 2.5, −4.3, −4.9, −5.0, −5.3
Preparation 23
Compound 402
Method: General Procedure 9
Starting material: Compound 401
Alkylating agent: Methyl iodide
Chromatography eluant: 0% to 1% ether in petroleum ether.
$^{13}$C NMR δ 148.2, 140.6, 134.9, 122.9, 117.8, 111.0, 83.9, 80.8, 80.4, 73.6, 71.8, 71.7, 67.4, 56.0, 55.8, 51.4, 45.8, 45.3, 44.6, 40.4, 39.4, 29.1, 28.7, 26.5, 25.9, 25.7, 25.6, 25.3, 23.3, 21.8, 19.2, 18.0, 18.0, 17.4, 13.8, 12.4, 7.6, 2.5, −4.4, −4.9, −5.0, −5.3
Preparation 24
Compound 403
Method: General Procedure 9
Starting material: Compound 401
Alkylating agent: Ethyl bromide
Chromatography eluant: 0% to 1% ether in petroleum ether.
$^{13}$C NMR δ 148.2, 140.7, 134.8, 123.0, 117.7, 111.0, 83.3, 81.4, 80.4, 72.0, 71.8, 71.7, 67.4, 63.8, 55.9, 51.4, 45.8, 45.4, 44.6, 40.3, 39.3, 29.1, 28.7, 26.4, 25.9, 25.7, 25.6, 25.3, 23.3, 21.8, 18.1, 18.0, 17.4, 15.0, 13.9, 12.4, 7.6, 2.5, −4.4, −4.9, −5.0, −5.3
Preparation 25
Compound 404
Method: General Procedure 9
Starting material: Compound 401
Alkylating agent: Propyl bromide
Chromatography eluant: 0% to 1% ether in petroleum ether.
$^{13}$C NMR δ 148.2, 140.8, 134.8, 123.0, 117.7, 111.0, 83.3, 81.5, 80.5, 72.1, 71.8, 71.7, 70.1, 67.4, 55.9, 51.4, 45.8, 45.4, 44.6, 40.4, 39.5, 29.1, 28.7, 26.3, 25.9, 25.7, 25.6, 25.3, 23.3, 22.9, 21.8, 18.0, 18.0, 17.3, 13.9, 12.4, 10.7, 7.6, 2.5, −4.4, −4.9, −5.0, −5.3
Preparation 26
Compound 405
Method: General Procedure 9
Starting material: Compound 401
Alkylating agent: Benzyl bromide
Chromatography eluant: 0% to 1% ether in petroleum ether.
$^{13}$C NMR δ 148.2, 140.7, 138.5, 134.9, 128.2, 128.0, 127.6, 127.4, 127.1, 122.9, 117.7, 111.0, 84.1, 81.0, 80.4, 71.8, 71.7, 70.1, 67.4, 55.8, 51.4, 45.8, 45.4, 44.6, 40.4, 39.4, 29.2, 28.7, 26.3, 25.9, 25.7, 25.6, 25.3, 23.2, 21.8, 18.0, 18.0, 17.4, 14.0, 12.4, 7.7, 2.5, −4.4, −4.8, −4.9, −5.0, −5.3
Preparation 27
Compound 303
Method: General Procedure 7
Starting material: Compound 208
Chromatography eluant: 0% to 5% ether in petroleum ether.
$^{13}$C NMR δ 153.4, 142.8, 135.3, 121.5, 116.4, 106.5, 83.1, 82.9, 80.0, 77.0, 72.9, 70.1, 67.0, 64.6, 56.0, 51.4, 45.5, 43.8, 41.0, 39.6, 36.4, 28.7, 28.0, 27.2, 26.4, 25.8, 25.7, 25.7, 25.6, 23.2, 21.9, 18.1, 17.9, 17.7, 13.0, 12.4, 8.4, 2.5, −4.4, −5.0, −5.1, −5.1
Preparation 28
Compound 406
Method: General Procedure 8
Starting material: Compound 303
Chromatography eluant: 0% to 5% ether in petroleum ether.
$^{13}$C NMR δ 148.2, 140.5, 135.0, 122.9, 117.9, 111.0, 83.1, 82.9, 80.0, 72.9, 71.8, 67.3, 64.6, 55.9, 51.4, 45.8, 45.3, 44.6, 41.0, 39.7, 28.6, 28.0, 27.2, 26.5, 25.8, 25.7, 25.7, 25.6, 23.2, 21.8, 18.0, 17.9, 17.9, 17.7, 13.0, 12.3, 8.4, 2.5, −4.4, −4.9, −4.9, −5.0, −5.3
Preparation 29
Compound 407
Method: General Procedure 9
Starting material: Compound 406
Alkylating agent: Ethyl bromide
Chromatography eluant: 0% to 2% ether in petroleum ether.
13C NMR δ 148.2, 140.8, 134.8, 123.0, 117.7, 111.0, 83.1, 81.4, 80.1, 72.9, 71.9, 71.8, 67.4, 63.8, 55.9, 51.4, 45.8, 45.4, 44.6, 40.4, 39.4, 28.7, 28.0, 27.2, 26.5, 25.8, 25.7, 25.6, 23.3, 21.8, 18.0, 18.0, 17.9, 17.7, 15.0, 13.9, 12.4, 8.3, 2.4, −4.4, −4.9, −4.9, −5.0, −5.3

Preparation 30
Compound 304
Method: General Procedure 7
Starting material: Compound 210
Chromatography eluant: 5% ether in petroleum ether.
$^{13}$C NMR δ 153.4, 142.8, 135.3, 121.5, 116.4, 106.5, 83.2, 82.9, 80.3, 71.6, 70.1, 67.0, 64.6, 56.0, 51.4, 45.5, 43.8, 41.0, 39.6, 36.4, 28.9, 28.7, 26.4, 25.8, 25.7, 25.6, 25.2, 23.2, 21.9, 18.1, 18.0, 17.9, 17.3, 13.0, 12.4, 7.6, 2.5, −4.3, −4.9, −5.0, −5.1, −5.1

Preparation 31
Compound 408
Method: General Procedure 8
Starting material: Compound 304
Chromatography eluant: 5% ether in petroleum ether.
$^{13}$C NMR δ 148.2, 140.4, 135.0, 122.9, 117.9, 111.0, 83.1, 83.0, 80.3, 71.8, 71.6, 67.3, 64.9, 55.9, 51.4, 45.8, 45.3, 44.6, 41.0, 39.7, 28.9, 28.6, 26.5, 25.8, 25.7, 25.7, 25.6, 25.2, 23.2, 21.8, 18.0, 17.9, 17.3, 13.0, 12.3, 7.6, 2.5, −4.3, −4.9, −5.0, −5.3

Preparation 32
Compound 409
Method: General Procedure 9
Starting material: Compound 408
Alkylating agent: Ethyl bromide
Chromatography eluant: 1% ether in petroleum ether.
$^{13}$C NMR δ 148.2, 140.7, 134.8, 123.0, 117.7, 111.0, 83.4, 81.4, 80.4, 72.0, 71.8, 71.7, 67.8, 67.4, 63.8, 55.9, 51.3, 45.8, 45.4, 44.6, 40.3, 39.3, 29.0, 28.7, 26.3, 25.8, 25.7, 25.6, 25.4, 25.3, 23.3, 21.8, 18.0, 18.0, 17.4, 15.0, 14.0, 12.4, 7.6, 2.5, −4.4, −4.9 −5.0, −5.3

Preparation 33
Compound 305
Method: General Procedure 7
Starting material: Compound 212
Chromatography eluant: 3% ether in petroleum ether.
$^{13}$C NMR δ 263.2, 153.4, 142.8, 135.3, 121.5, 116.4, 106.5, 82.9, 80.0, 72.9, 70.1, 67.0, 64.7, 56.0, 51.4, 45.5, 43.8, 41.0, 39.6, 36.4, 28.7, 28.0, 27.2, 26.4, 25.7, 25.7, 25.6, 23.2, 21.9, 18.1, 17.9, 17.6, 13.0, 12.4, 8.4, 2.5, −4.4, −5.0, −5.1

Preparation 34
Compound 410
Method: General Procedure 8
Starting material: Compound 305
Chromatography eluant: 3% ether in petroleum ether.
$^{13}$C NMR δ 148.2, 140.5, 135.0, 122.9, 117.9, 111.0, 83.1, 82.9, 80.0, 72.9, 71.8, 67.3, 64.7, 55.9, 51.4, 45.8, 45.3, 44.6, 41.0, 39.7, 28.7, 28.0, 27.2, 26.5, 25.7, 25.7, 25.6, 23.2, 21.8, 18.1, 18.0, 17.9, 17.6, 13.0, 12.3, 8.4, 2.5, −4.4, −4.9, −4.9, −5.0, −5.3

Preparation 35
Compound 411
Method: General Procedure 9
Starting material: Compound 410
Chromatography eluant: 1% ether in petroleum ether.
$^{13}$C NMR δ 148.2, 140.8, 134.8, 123.0, 117.7, 111.0, 83.0, 81.4, 80.1, 72.9, 72.0, 71.8, 67.4, 63.8, 55.9, 51.4, 45.8, 45.4, 44.7, 40.3, 39.3, 28.7, 28.0, 27.2, 26.4, 25.8, 25.7, 25.6, 23.3, 21.8, 18.0, 18.0, 17.9, 17.6, 15.0, 14.0, 12.4, 8.4, 2.5, −4.4, −4.9, −4.9, −5.0, −5.3

Preparation 36
Compound 306
Method: General Procedure 7a
Starting material: Compound 216
Chromatography eluant: 0% to 20% ether in petroleum ether.
$^{13}$C NMR δ 153.4, 142.7, 135.4, 121.5, 116.4, 108.1, 106.5, 85.6, 84.8, 79.3, 78.9, 70.1, 67.0, 64.4, 55.9, 51.2, 45.5, 43.8, 40.6, 39.5, 36.4, 28.7, 28.2, 28.0, 26.2, 25.9, 25.7, 25.6, 23.2, 21.9, 18.1, 17.9, 13.5, 13.1, 12.4, 8.2, −5.0, −5.1, −5.1

Preparation 37
Compound 412
Method: General Procedure 8
Starting material: Compound 306
Chromatography eluant: 10% ether in petroleum ether.
$^{13}$C NMR δ 148.1, 140.3, 135.0, 122.9, 117.9, 111.0, 108.1, 85.6, 84.7, 79.3, 78.9, 71.9, 67.3, 64.4, 55.8, 51.2, 45.8, 45.3, 44.6, 40.6, 39.5, 28.6, 28.2, 28.0, 26.2, 25.9, 25.7, 25.6, 23.1, 21.8, 18.0, 17.9, 13.5, 13.1, 12.4, 8.2, −4.9, −5.0, −5.3

Preparation 38
Compound 413
Method: General Procedure 9
Starting material: Compound 412
Alkylating agent: Ethyl bromide
Chromatography eluant: 0% to 2% ether in petroleum ether.
$^{1}$H NMR δ 6.22 (d,1H), 6.00 (d,1H), 5.17 (d,1H), 4.85 (d,1H), 4.36 (m,1H), 4.30 (q,1H), 4.20 (d,1H), 4.16 (m,1H), 3.72 (m,1H), 3.30 (m,1H), 2.82 (dd,1H), 2.43 (dd,1H), 2.20 (dd,1H), 1.99 (t,1H), 2.0–0.8 (m,15H), 1.44 (s,3H), 1.40 (s,3H), 1.26 (d,3H), 1.18 (t,3H), 1.07 (t,3H), 1.00 (d,3H), 0.87 (s,18H), 0.51 (s,3H), 0.05 (s,12H)

Preparation 39
Compound 307
Method: General Procedure 7a
Starting material: Compound 220
Chromatography eluant: 0% to 20% ether in petroleum ether.
$^{13}$C NMR δ 153.4, 142.7, 135.3, 121.5, 116.4, 108.2, 106.5, 87.9, 83.8, 81.2, 78.4, 70.1, 67.0, 64.4, 55.9, 51.3, 45.4, 43.8, 40.7, 39.5, 36.4, 31.3, 28.7, 27.6, 26.8, 26.3, 25.7, 25.6, 23.2, 21.9, 18.1, 17.9, 15.8, 13.1, 12.4, 8.7, −5.0, −5.1, −5.1

Preparation 40
Compound 414
Method: General Procedure 8
Starting material: Compound 307
No Chromatography: Crude product used in the next step
$^{13}$C NMR δ 6.22 (1H,d), 6.01 (1H,d), 5.17 (1H,d), 4.85 (1H,d), 4.67 (1H,s), 4.36 (1H,m), 4.17 (1H,m), 3.85 (1H,q), 2.82 (1H,dd), 2.43 (1H,dd), 2.21 (1H,dd), 1.89 (1H,t), 1.85–1.00 (13H,m), 1.68 (2H,q), 1.51 (3H,s), 1.35 (3H,d), 1.33 (3H,s), 1.06 (3H,t), 1.04 (3H,d), 0.87 (18H, s), 0.53 (3H,s), 0.05 (12H,s)

Preparation 41
Compound 415
Method: General Procedure 9
Starting material: Compound 414
Alkylating agent: Ethyl bromide
Chromatography eluant: 0% to 2% ether in petroleum ether.
$^{13}$C NMR δ 148.1, 140.7, 134.9, 122.9, 117.8, 111.0, 108.1, 86.5, 84.2, 81.3, 78.5, 71.9, 71.8, 67.3, 63.9, 55.9, 51.4, 45.9, 44.6, 40.2, 39.3, 31.4, 28.7, 27.5, 26.9, 26.3, 25.7, 25.6, 23.3, 21.8, 18.0, 18.0, 15.8, 15.0, 14.0, 12.4, 8.8, −4.9, −5.0, −5.3

Preparation 42
Compound 505
Method: General Procedure 11
Starting material: Methyl (R)-(+)-lactate
Purification: Distillation; b.p. 94° C./1.3 mbar; $[\alpha]_D^{20}$+54.4° (c 2.29, CHCl$_3$)
$^{13}$C NMR δ 170.0, 74.1, 52.8, 39.1, 18.4

Preparation 43
Compound 506
Method: General Procedure 11
Starting material: Ethyl (S)-(−)-lactate
Purification: Distillation; b.p. 98° C./1.5 mbar; $[\alpha]_D^{20}$−53.1° (c 2.03, CHCl$_3$), (litt.:
Breitschuh, R. et al., Synthesis, 1992, 1170: $[\alpha]_D^{20}$−54.6° (c 4.36. CHCl$_3$))

Preparation 44
Compound 507
Method: General Procedure 12
Starting material: Compound 505
Purification: Distillation; b.p. 39° C./53 mbar; $[\alpha]_D^{20}$−2.8° (c 2.21, CHCl$_3$)
$^1$H NMR δ 5.02 (dq,1H), 3.80 (s,3H), 1.58 (dd,3H)

Preparation 45
Compound 508
Method: General Procedure 12
Starting material: Compound 506
Purification: Distillation; b.p. 34° c./27 mbar; $[\alpha]_D^{20}$+3.8° (c 2.32, CHCl$_3$)
$^{13}$C NMR δ 170.5, 85.7, 61.5, 18.3, 14.1

Preparation 46
Compound 509
Method: General Procedure 1a
Starting material: Compound 507
Purification: Distillation; b.p. about 45° C./27 mbar; $[\alpha]_D^{20}$−51.6° (approx.) (c 2.1, CHCl$_3$:THF 4:1)
$^1$H NMR δ 4.88 (dq, 1H); 2.64 (m, 2H); 1.47 (dd, 3H); 1.08 (t, 3H)

Preparation 47
Compound 510
Method: General Procedure 1a
Starting material: Compound 508
Purification: Distillation; b.p. about 45° C./27 mbar; $[\alpha]_D^{20}$+43.3° (approx.) (c 2.0, CHCl$_3$:THF 7:3)
$^{13}$C NMR δ 210.8, 92.6, 30.7, 17.7, 6.8

Preparation 48
Compound 221
Method: General Procedure 2a
Purification: None
Starting material: Compound 509
$^{13}$C NMR δ
  Major 93.4, 79.6, 74.3, 71.3, 27.8, 25.0, 14.8, 7.4
  Minor 93.0, 80.0, 74.6, 71.0, 27.0, 25.4, 14.7, 7.2

Preparation 49
Compound 222
Method: General Procedure 6
Starting material: Compound 221
Chromatography eluant: petroleum ether Preparation 50
Compound 223
Method: General Procedure 2a
Starting material: Compound 210
Purification: None
$^{13}$C NMR δ
  Major: 93.4, 79.7, 74.3, 71.4, 27.8, 25.0, 14.8, 7.4
  Minor: 93.0, 80.0, 74.8, 71.0, 27.0, 25.4, 14.7, 7.2

Preparation 51
Compound 224
Method: General Procedure 6
Starting material: Compound 223
Chromatography eluant: petroleum ether.
$^{13}$C NMR δ
  Major: 93.2, 80.4, 78.3, 70.5, 28.1, 25.9, 14.9, 7.7, 2.1
  Minor: 92.5, 80.6, 78.2, 70.3, 27.9, 25.1, 14.6, 7.2, 2.1

Preparation 52
Compound 308
Method: General Procedure 7
Starting materials: Compound 1 and Compound 222
Chromatography eluant: 0% to 20% ether in petroleum ether Preparation 53
Compound 416
Method: General Procedure 8a
Starting material: Compound 308
Chromatography eluant: 50% dichloromethane in petroleum ether Preparation 54
Compound 417
Method: General Procedure 9
Starting material: Compound 416
Alkylating agent: Ethyl bromide
Chromatography eluant: 0% to 10% ether in petroleum ether Preparation 55
Compound 309
Method: General Procedure 7
Starting materials: Compound 1 and Compound 224
Chromatography eluant: 0% to 20% ether in petroleum ether.
$^{13}$C NMR δ 153.4, 142.7, 135.4, 121.5, 116.4, 106.5, 93.3, 83.1, 81.5, 78.5, 70.1, 67.0, 64.6, 55.9, 51.4, 45.5, 43.8, 41.2, 40.9, 39.6, 36.4, 28.9, 28.7, 28.3, 27.5, 26.3, 25.7, 25.6, 23.2, 22.4, 21.9, 20.2, 19.2, 18.1, 17.9, 15.1, 14.8, 14.1, 13.0, 12.4, 11.2, 7.8, 2.2, −5.0, −5.1, −5.1

Preparation 56
Compound 418
Method: General Procedure 8a
Starting material: Compound 309
Chromatography eluant: 50% dichloromethane in petroleum ether.
$^1$H NMR δ 6.22 (d,1H), 6.02 (d,1H), 5.17 (d,1H), 4.85 (d,1H), 4.62 (dq,1H), 4.60 (m,1H), 4.37 (m,1H), 4.18 (m,1H), 2.83 (d,1H, 2.50–0.80 (m,24H), 1.31 (dd,3H), 1.01 (d,3H), 0.85 (s,18H), 0.83 (d,3H), 0.12 (s,9H), 0.06 (d,12H)

Preparation 57
Compound 419
Method: General Procedure 9
Starting material: Compound 418
Alkylating agent: Ethyl bromide
Chromatography eluant: 0% to 10% ether in petroleum ether.
$^{13}$C NMR δ 148.1, 140.6, 134.9, 122.9, 117.8, 111.0, 93.4, 82.6, 80.5, 74.3, 71.9, 67.3, 64.0, 55.8, 51.3, 45.9, 45.4, 40.1, 39.3, 28.7, 27.8, 25.7, 25.6, 25.0, 23.3, 21.8, 18.0, 17.9, 14.7, 14.0, 12.4, 7.2, 2.2, −4.9, −5.0, −5.3

EXAMPLES

Example 1

1(S),3(R)-Dihydroxy-20(R)-(5-Ethyl-1(S),5(S), 6(S)-Trihydroxy-2-Heptyn-1-Yl)-9,10-Secopregna-5(Z), 7(E), 10(19)-Triene Compound 101
Method: General Procedure 4
Starting material: Compound 401
Chromatography eluant: 50% to 0% petroleum ether in ethyl acetate.
$^{13}$C NMR (CD$_3$OD) δ 149.8, 142.5, 135.8, 124.9, 119.0, 112.1, 84.3, 82.4, 77.1, 71.6, 71.5, 67.4, 65.5, 57.3, 52.7, 46.9, 46.2, 43.7, 42.4, 40.9, 30.1, 28.5, 27.0, 26.2, 24.5, 23.2, 17.3, 14.0, 13.1, 7.9

Example 2

1(S),3(R)-Dihydroxy-20(R)-(5(S),6(S)-Dihydroxy-5-Ethyl-1(S)-Methoxy-2-Heptyn-1-Yl)-9,10-Secopregna-5(Z), 7(E), 10(19)-Triene Compound 102
Method: General Procedure 4
Starting material: Compound 402
Chromatography eluant: 50% to 0% petroleum ether in ethyl acetate.
$^{13}$C NMR δ 147.7, 142.9, 133.1, 124.9, 117.2, 111.8, 82.4, 82.0, 75.6, 73.8, 71.3, 70.9, 66.8, 56.4, 56.0, 51.5, 45.7, 45.3, 42.9, 40.3, 39.4, 29.1, 27.2, 26.5, 26.4, 23.5, 22.1, 17.1, 14.1, 12.6, 7.7

Example 3

1(S),3(R)-dihydroxy-20(R)-(5(S),6(S)-Dihydroxy-1(S)-Ethoxy-5-Ethyl-2-Heptyn-1-Yl)-9,10-Secopregna-5(Z),7(E),10(19)-Triene Compound 103
Method: General Procedure 4
Starting material: Compound 403
Chromatography eluant: 50% to 0% petroleum ether in ethyl acetate.
$^{13}$C NMR δ 147.7, 142.9, 133.2, 124.8, 117.2, 111.8, 82.6, 81.9, 75.6, 72.3, 71.3, 70.8, 66.8, 64.2, 56.0, 51.5, 45.8, 45.3, 40.2, 39.3, 29.1, 27.2, 26.4, 26.3, 23.5, 22.2, 17.1, 15.2, 14.2, 12.7, 7.7

Example 4

1(S),3(R)-Dihydroxy-20(R)-(5(S),6(S)-Dihydroxy-5-Ethyl-1(S)-(1-n-Propyloxy)-2-Heptyn-1-Yl)-9,10-Secopregna-5(Z),7(E),10(19)-Triene Compound 104
Method: General Procedure 4
Starting material: Compound 404
Chromatography eluant: 50% to 0% petroleum ether in ethyl acetate.
$^{13}$C NMR δ 147.7, 143.0, 133.0, 125.0, 117.1, 111.8, 82.9, 81.7, 75.6, 72.4, 71.3, 70.9, 70.5, 66.9, 56.0, 51.5, 45.8, 45.3, 42.9, 40.3, 39.5, 29.1, 27.2, 26.5, 26.3, 23.5, 23.1, 22.2, 17.1, 14.2, 12.7, 10.9, 7.7

Example 5

1(S),3(R)-Dihydroxy-20(R)-(1(S)-Benzyloxy-5(S),6(S)-Dihydroxy-5-Ethyl-2-Heptyn-1-Yl)-9,10-Secopregna-5(Z), 7(E),10(19)-Triene Compound 105
Method: General Procedure 4
Starting material: Compound 405
Chromatography eluant: 50% to 0% petroleum ether in ethyl acetate.
$^{13}$C NMR δ 147.7, 142.9, 138.5, 133.1, 128.2, 127.7, 127.4, 124.9, 117.1, 111.8, 82.6, 82.2, 75.6, 71.9, 71.3, 70.8, 70.4, 66.8, 56.0, 51.5, 45.8, 45.3, 42.9, 40.3, 39.4, 29.0, 27.2, 26.4, 26.3, 23.5, 22.1, 20.8, 17.1, 12.7, 7.7

Example 6

1(S),3(R)-Dihydroxy-20(R)-(5(R),6(S)-Dihydroxy-1(S)-Ethoxy-5-Ethyl-2-Heptyn-1-Yl)-9,10-Secopregna-5(Z),7(E),10(19)-Triene Compound 106
Method: General Procedure 4
Starting material: Compound 407
Chromatography eluant: 50% to 0% petroleum ether in ethyl acetate.
$^{13}$C NMR δ 147.7, 142.8, 133.2, 124.8, 117.2, 111.8, 82.9, 81.9, 75.4, 72.3, 71.2, 70.8, 66.8, 64.2, 56.0, 51.5, 45.8, 45.2, 42.9, 40.2, 39.3, 29.2, 29.1, 26.2, 25.1, 23.5, 22.2, 17.1, 15.2, 14.2, 12.7, 7.5

Example 7

1(S),3(R)-Dihydroxy-20(R)-(5(R),6(R)-Dihydroxy-1(S)-Ethoxy-5-Ethyl-2-Heptyn-1-Yl)-9,10-Secopregna-5(Z), 7(E),10(19)-Triene Compound 107
Method: General Procedure 4
Starting material: Compound 409
Chromatography eluant: 50% to 0% petroleum ether in ethyl acetate.
$^{13}$C NMR δ147.7, 142.9, 133.2, 124.9, 117.2, 111.8, 82.6, 81.9, 75.6, 72.3, 71.3, 70.8, 66.8, 64.2, 56.0, 51.5, 45.8, 45.2, 42.8, 40.2, 39.3, 29.1, 27.2, 26.4, 26.3, 23.5, 22.1, 17.1, 15.2, 14.2, 12.7, 7.7

Example 8

1(S),3(R)-Dihydroxy-20(R)-(5(S),6(R)-Dihydroxy-1(S)-Ethoxy-5-ethyl-2-Heptyn-1-Yl)-9,10-Secopregna-5(Z),7E),10(19)-Triene Compound 108
Method: General Procedure 4
Starting material: Compound 411
Chromatography eluant: 50% to 0% petroleum ether in ethyl acetate.
$^{13}$C NMR δ 147.7, 142.8, 133.2, 124.8, 117.2, 111.8, 83.0, 81.9, 75.4, 72.3, 71.2, 70.8, 66.8, 64.2, 56.0, 51.5, 45.8, 45.2, 42.9, 40.2, 39.3, 29.3, 29.1, 26.3, 25.1, 23.5, 22.1, 17.1, 15.2, 14.2, 12.7, 7.5

Example 9

1(S),3(R)-Dihydroxy-20R)-(4-ethyl-1(S),4(S),5(S)-Trihydroxy-2-Hexyn-1-Yl)-9,10-Secopregna-5(Z), 7(E),10(19)-Triene Compound 109
Method: General Procedure 10
Starting material: Compound 412
Chromatography eluant: ethyl acetate.
$^{1}$H NMR (CD$_{3}$OD) δ 6.32 (d,1H), 6.08 (d,1H), 5.28 (d,1H), 4.90 (d,1H), 4.57 (d,1H), 4.35 (t,1H), 4.12 (m,1H), 3.63 (q,1H), 2.86 (dd,1H), 2.55 (dd,1H), 2.25 (dd,1H), 2.0–1.0 (m,16H), 1.27 (d,3H), 1.23 (d,3H), 1.05 (t,3H), 0.56 (s,3H)

Example 10

1(S),3(R)-Dihydroxy-20(R)-(4(S),5(S)-Dihydroxy-1(S)-Ethoxy-4-Ethyl-2-Hexyn-1-Yl)-9,10-Secopregna-5(Z),7(E),10(19)-Triene Compound 111
Method: General Procedure 10
Starting material: Compound 413
Chromatography eluant: 50% to 0% petroleum ether in ethyl acetate.
$^{1}$H NMR δ 6.37 (d,1H), 6.01 (d,1H), 5.32 (t,1H), 5.00 (d,1H), 4.42 (t,1H), 4.41 (m,2H), 3.81 (q,1H), 3.73 (m,1H), 3.31 (m,1H), 2.83 (dd,1H), 2.59 (dd,1H), 2.31 (m,2H), 2.1–1.0 (m,14H), 1.25 (d,3H), 1.21 (t,3H), 1.08 (t,3H), 1.02 (d,3H), 0.55 (s,5H)

Example 11

1(S),3(R)-Dihydroxy-20(R)-(4-Ethyl-1(S),4(R),5(S)-Trihydroxy-2-Hexyn-1-Yl)-9,10-Secopregna-5(Z), 7(E),10(19)-Triene Compound 114
Method: General Procedure 10
Starting material: Compound 414
Chromatography eluant: ethyl acetate.
$^{13}$C NMR δ (CD$_{3}$OD)149.9, 142.4, 135.8, 130.2, 124.9, 119.1, 112.1, 73.5, 71.5, 67.4, 65.3, 61.6, 57.3, 52.7, 46.9, 46.2, 43.8, 42.2, 40.9, 32.1, 30.1, 27.1, 24.6, 23.2, 18.3, 14.5, 14.0, 13.0, 9.0

Example 12

1(S),3(R)-Dihydroxy-20(R)-(4(R),5(S)-Dihydroxy-1(S)-Ethoxy-4-Ethyl-2-Hexyn-1-Yl)-9,10-Secopregna-5(Z),7(E),10(19)-Triene Compound 116
Method: General Procedure 10
Starting material: Compound 415
Chromatography eluant: 50% to 0% petroleum ether in ethyl acetate.
$^{13}$C NMR δ 147.6, 142.9, 133.0, 125.0, 117.1, 111.9, 85.8, 85.3, 75.5, 73.2, 72.0, 70.9, 66.9, 64.3, 56.0, 51.5, 45.7, 45.3, 42.9, 40.2, 39.4, 31.0, 29.1, 26.4, 23.5, 22.1, 18.5, 15.2, 14.2, 12.7, 8.3

Example 13

Capsules Containing Compound 103

Compound 103 was dissolved in arachis oil to a final concentration of 1 μg of Compound 103/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of Compound 103 in oil solution, such that each capsule contained 0.1 μg of Compound 103.

Example 14

Dermatological Cream Containing Compound 102

In 1 g almond oil was dissolved 0.05 mg of Compound 102. To this solution was added 40 g of mineral oil and 20 g of self-emulsifying beeswax. The mixture was heated to liquefy. After the addition of 40 ml hot water, the mixture was mixed well. The resulting cream contains approximately 0.5 μg of Compound 102 per gram of cream.

EXAMPLE 15

| Injection Fluid Containing Compound 108 | |
|---|---|
| Compound 108 (active substance) | 10 μg |
| Disodium phosphate dihydrate (buffer) | 5.4 mg |
| Sodium dihydrogen phosphate dihydrate (buffer) | 2 mg |
| Sodium chloride | 0.8 mg |
| Sodium ascorbate (antioxidant) | 5 mg |
| Solutol ® HS 15 from BASF (solubilizer) | 5 mg |
| Water for injection | ad 1 ml |

Solutol® HS 15 is dissolved in the water for injection by heating it to a temperature of at the most 80° C. A cover of nitrogen is applied. The buffer substances and the sodium chloride are added and then the solution is cooled to at the most 30° C. Then sodium ascorbate is added and, finally, compound 108 is dissolved in the solution obtained.

The solution is subjected to sterile filtration and is autoclaved at an appropriate time-temperature condition.

Example 16

1(S),3(R)-Dihydroxy-20(R)-(1(S),5(R/S)-Dihydroxy-5-Ethyl-6(S)-Fluoro-2-Heptyn-1-Yl)-9,10-Secopregna-5(Z),7(E),10(19)-Triene Compound 157
Method: General Procedure 10
Starting material: Compound 416
Chromatography eluant: 50% to 0% petroleum ether in ethyl acetate.

Example 17

1(S),3(R)-Dihydroxy-20(R)-(1(S)-ethoxy 5-ethyl-6(S)-Fluoro-2-Heptyn-5(R/S)-Hydroxy 1-Yl)-9,10-Secopregna-5(Z),7(E),10(19)-Triene Compound 158
Method: General Procedure 10
Starting material: Compound 417
Chromatography eluant: 50% petroleum ether in ethyl acetate.

Example 18

1(S),3(R)-Dihydroxy-20(R)-(1(S),5(R/S)-Dihydroxy-5-Ethyl-6(R)-Fluoro-2-Heptyn-1-Yl)-9,10-Secopregna-5(Z),7(E),10(19)-Triene Compound 159
Method: General Procedure 10
Starting material: Compound 418
Chromatography eluant: 50% to 0% petroleum ether in ethyl acetate.
$^{13}$C NMR δ 147.7, 142.7, 133.2, 134.9, 117.3, 111.8, 93.4, 84.2, 88.5, 74.5, 78.9, 66.9, 64.8, 56.0, 51.5, 45.7, 45.3, 42.9, 41.0, 39.6, 29.0, 28.0, 26.4, 25.3, 23.4, 22.1, 14.9, 13.3, 12.6, 7.5

Example 19

1(S),3(R)-Dihydroxy-20(R)-(1(S)-Ethoxy 5-Ethyl-6(R)-Fluoro-2-Heptyn-5(R/S)-Hydroxy 1-Yl)-9,10-Secopregna-5(Z),7(E),10(19)-Triene Compound 160
Method: General Procedure 10
Starting material: Compound 419
Chromatography eluant: 50% petroleum ether in ethyl acetate.
$^1$H NMR δ 6.37 (d,1H), 6.02 (d,1H), 5.33 (s,1H), 5.00 (s,1H), 4.68 (dq,1H), 4.43 (m,1H), 4.23 (m,1H), 4.13 (s,1H), 3.73 (m,1H), 3.30 (m,1H), 2.84 (dd,1H), 2.58 (m,2H), 2.40 (dd,1H), 2.31 (dd,1H), 2.05–1.20 (m,19H), 1.38 (dd,3H), 1.20 (t,3H),1.01 (d,3H), 0.96 (t,3H), 0.54 (s,3H)

What is claimed is:
1. A compound of the formula I

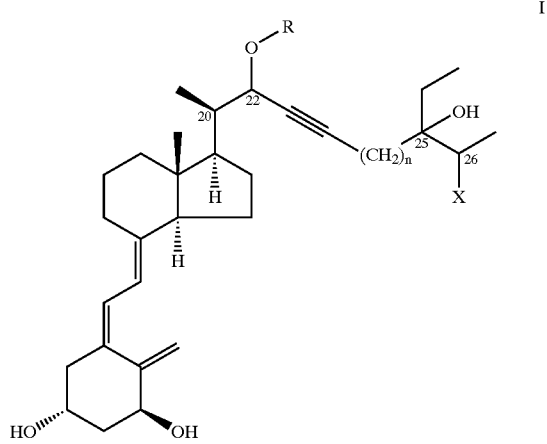

wherein R represents hydrogen, or R represents $(C_1–C_6)$ alkyl, phenyl, or $(C_7–C_9)$aralkyl, optionally substituted with one or more groups selected from $(C_1–C_3)$alkyl, F, and phenyl; n is an integer having the value 0, 1, or 2; and X represents hydroxy or halogen.

2. A compound according to claim 1 wherein R is selected from the group consisting of methyl, ethyl, propyl, isopropyl, benzyl, ortho methylbenzyl, meta methylbenzyl, and para methylbenzyl.

3. A compound according to claim 1 wherein n is 0 or 1.

4. A compound according to claim 1 wherein X represents a substituent selected from the group consisting of OH, F, and Cl.

5. A compound according to claim 1 having the configuration 22(S), 25(S), 26(S) or 22(S), 25(S), 26(R).

6. A compound according to claim 1 selected from the group consisting of

1(S),3(R)-Dihydroxy-20(R)-(5-ethyl-1(S),5(S),6(S)-trihydroxy-2-heptyn-1-yl)-9,10-secopregna-5(Z), 7(E), 10(19)-triene (Compound 101), 1(S),3(R)-Dihydroxy-20(R)-(5(S),6(S)-dihydroxy-5-ethyl-1(S)-methoxy-2-heptyn-1-yl)-9,10-secopregna-5(Z), 7(E),10(19)-triene (Compound 102), 1(S),3(R)-Dihydroxy-20(R)-5(S),6(S)-dihydroxy-1(S)-ethoxy-5-ethyl-2-heptyn-1-yl)-9,10-secopregna-5(Z), 7(E),10(19)-triene (Compound 103), 1(S),3(R)-Dihydroxy-20(R)-(5(S),6(S)-dihydroxy-5-ethyl-1(S)-(1-propyloxy)-2-heptyn-1-yl)-9,10-secopregna-5(Z), 7(E),10(19)-triene (Compound 104), 1(S),3(R)-Dihydroxy-20(R)-(1(S)-benzylyloxy-5(S),6(S)-dihydroxy-5-ethyl-2-heptyn-1-yl)-9,10-secopregna-5(Z), 7(E),10(19)-triene (Compound 105), 1(S),3(R)-Dihydroxy-20(R)-(5(R),6(S)-dihydroxy-1(S)-ethoxy-5-ethyl-2-heptyn-1-yl)-9,10-secopregna-5(Z), 7(E),10(19)-triene (Compound 106), 1(S),3(R)-Dihydroxy-20(R)-(5(R),6(R)-dihydroxy-1(S)-ethoxy-5-ethyl-2-heptyn-1-yl)-9,10-secopregna-5(Z), 7(E),10(19)-triene (Compound 107), 1(S),3(R)-Dihydroxy-20(R)-(5(R),6(R)-dihydroxy-1(S)-ethoxy-5-ethyl-2-heptyn-1-yl)-9,10-secopregna-5(Z), 7(E),10(19)-triene (Compound 108), (S),3(R)-Dihydroxy-20(R)-(4-ethyl-1(S),4(S),5(S)-trihydroxy-2-hexyn-1-yl)-9,10-secopregna-5(Z), 7(E), 10(19)-triene (Compound 109), (S),3(R)-Dihydroxy-20(R)-(4(S),5(S)-dihydroxy-1(S)-ethoxy-4-ethyl-2-hexyn-1-yl)-9,10-secopregna-5(Z), 7(E),10(19)-triene (Compound 111), 1(S),3(R)-Dihydroxy-20(R)-(4-ethyl-1(S),4(R),5(S)-trihydroxy-2-hexyn-1-yl)-9,10-secopregna-5(Z), 7(E), 10(19)-triene (Compound 114), 1(S),3(R)-Dihydroxy-20(R)-(4(R),5(S)-dihydroxy-1(S)-ethoxy-4-ethyl-2-hexyn-1-yl) 9,10-secopregna-5(Z),7(E),10(19)-triene (Compound 116), 1(S),3(R)-Dihydroxy-20(R)-(1(S)-ethoxy-5-ethyl-6(S)-fluoro-5(S)-hydroxy-2-heptyn-1-yl)-9,10-secopregna-5(Z), 7(E),10(19)-triene (compound 149), and 1(S),3(R)-Dihydroxy-20(R)-(1(S)-ethoxy-5-ethyl-6(R)-fluoro-5(S)-hydroxy-2-heptyn-1-yl)-9,10-secopregna-5(Z), 7(E),10(19)-triene (compound 150), 1(S),3(R)-Dihydroxy-20(R)-(1(S),5(R/S)-dihydroxy-5-ethyl-6(S)-fluoro-2-heptyn-1-yl)-9,10-secopregna-5(Z), 7(E),10(19)-triene (compound 157)

1(S),3(R)-Dihydroxy-20(R)-(1(S)-ethoxy 5-ethyl-6(S)-fluoro-2-heptyn-5(R/S)-hydroxy 1-yl)-9,10-secopregna-5(Z),7(E),10(19)-triene (compound 158)

1(S),3(R)-Dihydroxy-20(R)-(1(S),5(R/S)-dihydroxy-5-ethyl-6(R)-fluoro-2-heptyn-1-yl)-9,10-secopregna-5(Z), 7(E),10(19)-triene (compound 159)

1(S),3(R)-Dihydroxy-20(R)-(1(S)-ethoxy 5-ethyl-6(R)-fluoro-2-peptyn-5(R/S)-hydroxy 1-yl)-9,10-secopregna-5(Z),7(E),10(19)-triene (compound 160).

7. A method for producing a compound of formula I of claim 1 characterized in a) reacting 1(S),3(R)-bis-(tert-butyldimethylsilyloxy)-20(R)-formyl-9,10-secopregna-5(E), 7(E),10(19)-triene, with an organometallic reagent derived from the side chain building block HC≡C—(CH$_2$)$_n$—C(C$_2$H$_5$)(O—PG$^1$)(CHX$^1$—CH$_3$), wherein n and R have the meanings specified above; X$^1$ represents O—PG$^2$, fluorine, chlorine, bromine, or iodine; PG$^1$ and PG$^2$ both represent the same or different group selected from trimethylsilyl and tert-butyl-dimethylsilyl; or PG$^1$ and PG$^2$ together form one bifunctional isopropylidene ketal protective group; to form a compound of formula III, and b) optionally separating from diastereoisomers the compound formed in step a), c) subjecting the compound formed in step a) or step b) to triplet-sensitized photo-isomerization to the 5(Z) isomer, d) optionally alkylating the compound formed in step c) at the 22-hydroxy group with a (C$_1$–C$_6$)alkyl or (C$_7$–C$_9$)aralkyl bromide or iodide in the presence of a base and a phase transfer catalyst, and e) deprotecting the compound formed in step c) or step d) to form a compound of formula I.

8. A pharmaceutical composition containing an effective amount of one or more of the compounds of claim 1, together with pharmaceutically acceptable, non-toxic carriers and/or auxiliary agents.

9. A compound according to claim 1 wherein n is 1.

10. A method of inhibiting proliferation of leukaemia cells, breast cancer cells and skin cells, the method comprising contacting said cells with an effective amount of a compound according to claim 1, optionally in combination with other therapeutically active compounds.

11. A compound according to claim 1 wherein the compound is a diastereoisomer of formula I.

12. A compound according to claim 1 wherein the compound is a diastereoisomer of formula I in pure form.

13. A compound according to claim 1 wherein the compound comprises a mixture of diastereoisomers of formula I.

14. A compound according to claim 3 wherein n is 1.

* * * * *